(12) United States Patent
Eshima et al.

(10) Patent No.: US 10,111,955 B2
(45) Date of Patent: Oct. 30, 2018

(54) PEG DERIVATIVE

(71) Applicant: Delta-Fly Pharma, Inc., Tokushima-shi (JP)

(72) Inventors: Kiyoshi Eshima, Tokushima (JP); Masakazu Fukushima, Otsu (JP)

(73) Assignee: Delta-Fly Pharma, Inc., Tokushima-shi (JP)

( * ) Notice: Subject to any disclaimer, the term of this patent is extended or adjusted under 35 U.S.C. 154(b) by 0 days.

(21) Appl. No.: 15/520,956

(22) PCT Filed: Dec. 3, 2015

(86) PCT No.: PCT/JP2015/084068
§ 371 (c)(1),
(2) Date: Apr. 21, 2017

(87) PCT Pub. No.: WO2016/088858
PCT Pub. Date: Jun. 9, 2016

(65) Prior Publication Data
US 2017/0368177 A1    Dec. 28, 2017

(30) Foreign Application Priority Data

Dec. 4, 2014    (JP) .................. 2014-246110

(51) Int. Cl.
*A61K 47/10* (2017.01)
*A61K 31/407* (2006.01)
(Continued)

(52) U.S. Cl.
CPC ............ *A61K 47/10* (2013.01); *A61K 31/407* (2013.01); *A61K 31/496* (2013.01);
(Continued)

(58) Field of Classification Search
CPC ..................................................... A61K 47/10
See application file for complete search history.

(56) References Cited

U.S. PATENT DOCUMENTS 5,770,599 A    6/1998  Gibson
6,376,470 B1   4/2002  Greenwald et al.
(Continued)

FOREIGN PATENT DOCUMENTS

JP    11-504033 A     4/1999
JP    2003-524028 A   8/2003
(Continued)

OTHER PUBLICATIONS

Pinedo et al. (2000).*
(Continued)

*Primary Examiner* — Paul V Ward
(74) *Attorney, Agent, or Firm* — Oblon, McClelland, Maier & Neustadt, L.L.P.

(57) ABSTRACT

Provided is a new therapeutic agent for a malignant tumor, which is highly safe, sustains an antitumor effect, and can improve the means for administration and the number of times of administration. Disclosed is a compound of Formula (1), or a salt thereof:

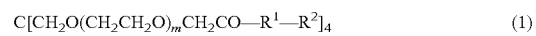

wherein $R^1$ represents a single bond, $-N(R^3)(CH_2)_{n1}CO-$, or $-N(R^4)(CH_2)_{n2}N(R^5)CO(CH_2)_{n3}CO-$;

$R^2$ represents a group of Formula (a), (b), (c), (d), (e), or (f):

(Continued)

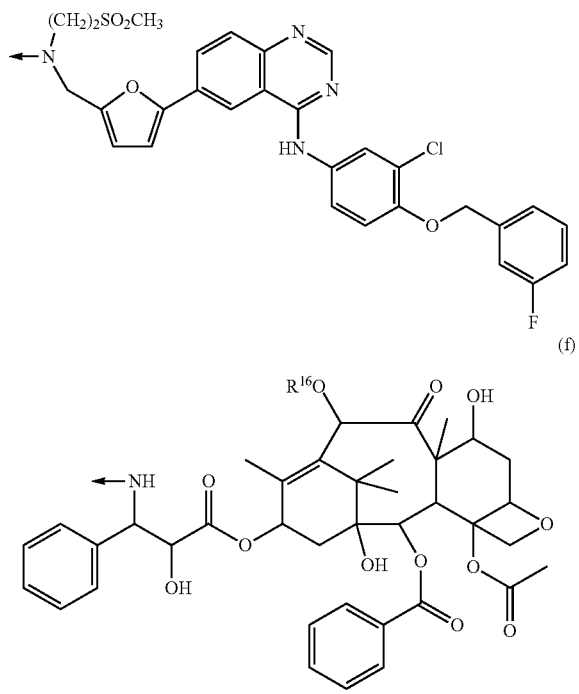

m represents a number of from 10 to 1,000; and an arrow represents a bonding site.

8 Claims, 13 Drawing Sheets

(51) Int. Cl.
| | |
|---|---|
| A61K 31/496 | (2006.01) |
| A61K 31/7068 | (2006.01) |
| C08G 65/333 | (2006.01) |
| G01R 33/46 | (2006.01) |
| A61K 31/77 | (2006.01) |

(52) U.S. Cl.
CPC ........ *A61K 31/7068* (2013.01); *C08G 65/333* (2013.01); *A61K 31/77* (2013.01); *G01R 33/46* (2013.01)

(56) References Cited

U.S. PATENT DOCUMENTS

| 8,962,566 B2 | 2/2015 | Kozlowski et al. |
|---|---|---|
| 2001/0051144 A1 | 12/2001 | Greenwald et al. |
| 2005/0112088 A1 | 5/2005 | Zhao et al. |
| 2008/0194612 A1 | 8/2008 | Zhao et al. |
| 2009/0074704 A1 | 3/2009 | Zhao et al. |
| 2010/0152414 A1 | 6/2010 | Zhao et al. |
| 2010/0190933 A1 | 7/2010 | Zhao et al. |
| 2011/0200550 A1 | 8/2011 | Kozlowski et al. |
| 2012/0238621 A1 | 9/2012 | Riggs-Sauthier et al. |
| 2013/0143909 A1 | 6/2013 | Chong et al. |
| 2013/0158062 A1 | 6/2013 | Zhao et al. |
| 2013/0231359 A1 | 9/2013 | Chong et al. |
| 2014/0323514 A1 | 10/2014 | Zhao et al. |
| 2015/0105519 A1 | 4/2015 | Chong et al. |
| 2015/0133534 A1 | 5/2015 | Kozlowski et al. |

FOREIGN PATENT DOCUMENTS

| JP | 2007-505928 A | 3/2007 |
|---|---|---|
| JP | 2011-530597 A | 12/2011 |
| JP | 2013-511540 A | 4/2013 |
| WO | 2009/123768 | 10/2009 |
| WO | 2011/130599 | 10/2011 |
| WO | 2012/088522 | 6/2012 |
| WO | 2012/098557 | 7/2012 |
| WO | 2015/049883 | 4/2015 |

OTHER PUBLICATIONS

McMahon et al. (2000).*
International Search Report dated Feb. 2, 2016, in PCT/JP2015/084068 filed Dec. 3, 2015.
Communications to the Editor, Journal of Medicinal Chemistry, vol. 34, (1991), pp. 2917-2919.
Azuma et al., "Nucleosides and Nucleotides. 122. 2'-C-Cyano 2'-deoxy-1-β-D-arabinofuranosylcytosine and Its Derivatives. A New Class of Nucleoside with a Broad Antitumor Spectrum", Journal of Medicinal Chemistry, vol. 36, (1993), pp. 4183-4189.
Package insert for CYLOCIDE™ Injections, "Cylocide Injection", (2014), 4 pages.
Partial European Search Report issued on Jun. 18, 2018 for European Patent Application No. 15864609.1.
Gianfranco Pasut, et al.,"Antitumoral activity of PEG-Gemcitabine prodrugs targeted by folic acid", Journal of Controlled Release, vol. 127, Issue 3, May 1, 2008, pp. 239-248.
O. Schiavon, et al., "PEG-Ara-C conjugates for controlled release", European Journal of Medicinal Chemistry, vol. 39, Issue 2, Feb. 1, 2004, pp. 123-133.
Yun H. Choe, et al., "Anticancer drug delivery systems: multi-loaded N4-acyl poly (ethylene glycol) prodrugs of ara-C.: II. Efficacy in ascites and solid tumors", Journal of Controlled Release, vol. 79, Issues 1-3, Feb. 19, 2002, pp. 55-70.
Manasmita Das, et al., "Macromolecular Bipill of Gemcitabine and Methotrexate Facilitates Tumor-Specific Dual Drug Therapy with Higher Benefit-to-Risk Ratio", Bioconjugate Chem., Mar. 19, 2014, 25 (3), pp. 501-509.
Gianfranco Pasut, et al., "Antitumoral activity of PEG-gemcitabine prodrugs targeted by folic acid" Journal of Controlled Release, vol. 127, Issue 3, May 1, 2008, pp. 239-248.

* cited by examiner

PEG DERIVATIVE

TECHNICAL FIELD

The present invention relates to a novel PEG derivative useful as a therapeutic agent for malignant tumors, and a pharmaceutical product containing the same.

BACKGROUND ART

Cytosine derivatives such as cytarabine, 1-(2'-cyano-2'-deoxy-β-D-arabinofuranosyl)cytosine, gemcitabine, decitabine, 5-azacitidine, RX-3117 (Rexahn), and SGI-110 (Astex), have effects of inhibiting cancer DNA polymerases or regulating the cancer cell cycle (G2/M arrest), and inducing differentiation of leukemic cells. Therefore, cytosine derivatives are useful as therapeutic agents for malignant tumors such as acute myelogenous leukemia, acute leukemia lymphocytic, malignant lymphoma, multiple myeloma, pancreatic cancer, lung cancer, and breast cancer (Patent Literature 1, Non-Patent Literatures 1 to 3). Therapy for malignant tumors using these cytosine derivatives involves administration of intravenous infusion that is usually sustained for several hours to several weeks (Non-Patent Literature 1).

Furthermore, mitomycin C is an anticancer agent used for the treatment of chronic lymphocytic leukemia, chronic myelogenous leukemia, gastric cancer, colorectal cancer, lung cancer, pancreatic cancer, liver cancer, cervical cancer, uterine cancer, head and neck tumor, and urinary bladder tumor. However, mitomycin C is also usually subjected to everyday intravenous administration. Gefitinib and erlotinib are molecular targeted anticancer agents that selectively inhibit tyrosine kinase of epithelial growth factor receptor (EGFR), and are used for, for example, non-small cell lung cancer, pancreatic cancer, glioblastosis cerebri, and head and neck squamous cell carcinoma. Furthermore, lapatinib and sunitinib are also tyrosine kinase inhibitors, and are used for, for example, breast cancer. However, these molecular targeted drugs also have a problem with adverse effects such as acute lung injury and interstitial pneumonitis.

Paclitaxel and docetaxel are anticancer agents used for the treatment of, for example, lung cancer, ovarian cancer, breast cancer, head and neck cancer, and progressive Kaposi's sarcoma. However, these taxane-based anticancer agents also have adverse effects such as myelosuppression such as leukopenia, and peripheral nerve disorder, and lack water-solubility. CREMOPHOR is obliged to be used as a dissolution aid, but since CREMOPHOR causes severe allergic symptoms, a pretreatment of histamine H1/H2 antagonists is indispensable, which requires complicated operations at administration in the clinical environment. Furthermore, there are occasions in which human serum albumin is used as a dissolution aid; however, there is a concern for risks such as lack of human serum albumin and viral infection such as AIDS.

Conventional anticancer agents formed from low molecular weight compounds have been clinically applied by intravenous administration or peroral administration; however, in the present circumstances they are still in low availability, and only an extremely small portion of the amount administered reaches tumors. In addition, the anticancer agents are systemically distributed, which leads to systemic toxicity. Since the dosage is determined by the balance between effect and toxicity, systemic toxicity occurs. Thus, in most cases, a sufficient amount of an anticancer agent required to exhibit the drug efficacy is not administered.

In recent years, several drug delivery systems have been developed for the purpose of overcoming the problems described above. For example, representative examples of drug delivery systems (hereinafter, referred to as DDS) include methods of physically embedding a low molecular weight anticancer agent in phospholipid liposomes, polymer micelles, or a water-soluble polymer, all of which are formed from biocompatible material components, or forming chemical covalent bonds between the two.

Regarding a liposome preparation for intravenous administration, since the particle size is controlled to be 200 to 300 nm so that liposomes can pass through capillary blood vessels without any problem and can pass through new blood vessels near a tumor, and in addition to that, since the membrane surface of the liposome particles is coated with a polyethylene glycol (hereinafter, referred to as PEG) having a molecular weight of about 2,000, ingestion of the liposomes by phagocytes in vivo is generally avoided.

In a polymer micelle preparation, since the particle size is controlled to 50 nm, and the membrane surface of the particles is coated with PEG, ingestion of the micelles by phagocytes in vivo can be generally avoided, and it has been reported that the polymer micelles can easily pass through new blood vessels near a tumor.

However, in the present circumstances, the above-mentioned preparations containing nano-sized fine particles have relatively short half-lives in blood, targeting to tumors is also unsatisfactory, and the intrinsic purpose is not sufficiently achieved.

Meanwhile, attempts have recently begun for clinical application of derivatives in which an anticancer agent is chemically covalently bonded to a synthetic high-molecular weight PEG having high biocompatibility and high water-solubility, particularly a PEG having four chains (molecular weight 40,000) that does not easily form a high viscosity solution.

CITATION LIST

Non-Patent Literature

Non-Patent Literature 1: J. Med. Chem., Vol. 34, 2917-2919 (1991)

Non-Patent Literature 2: J. Med. Chem., Vol. 36, 4183-4189 (1993)

Non-Patent Literature 3: package insert for CYLOCIDE™ injections

SUMMARY OF INVENTION

Technical Problem

However, since attention has been paid in excess to controlled release of the derivatives into the blood, the chemical bonding between PEG and the anticancer agent is limited to ester bonding or carbamate bonding, both of which are relatively easily decomposed by lyases such as esterases or carboxylases in the blood. Thus, long-term stability in blood is not sufficiently obtained, the targeting efficiency to tumor tissues is not satisfactory, and the original purpose of DDS is not attained.

Recently, it has been reported that a four-branched PEG and SN-38, which is an active ingredient of an anticancer agent (CPT-11), were covalently bonded by carbamate bonding that is not easily decomposed into an acid or an alkali; however, this merely overcomes the weak points of carbamate bonding to a certain extent. Furthermore, the conditions for the chemical reaction employed in synthesizing a carbamate-bonded body are harsh (strongly alkaline conditions), and the conditions are not suitable for intramolecular ester bonds or for the bonding of an anticancer agent that is sensitive to alkali.

Therefore, it is an object of the present invention to provide a new therapeutic agent for a malignant tumor, which has reduced adverse effects such as severe gastrointestinal toxicity or bone marrow toxicity, has a sustained antitumor effect, and enables improvements in the means for administration and the frequency of administration.

Solution to Problem

Thus, the inventors of the present invention paid attention to sustainability of a PEG derivative in blood and high clustering properties to tumor tissues, and in order to enhance the effect durability of an antitumor agent, the inventors conducted investigations in view of the controlled release properties in blood associated with lyases in blood, on the modification of SN-38, which is an active substance of CPT-11, by ester bonding or carbamate bonding between a hydroxyl group of SN-38 and polyethylene glycol. However, it was found that the antitumor active substance was released into blood faster than expected in human beings, a large amount of the polyethylene glycol derivative was required to administer, and sufficient effect durability enhancement or safety enhancement was not to be obtained.

Thus, the inventors further conducted investigations, and as a result, the inventors found that a compound of Formula (1), in which a four-branched polyethylene glycol having a methylcarboxyl group introduced into each of the chain terminals is amide-bonded to a primary or secondary amino group of an antitumor agent such as a cytosine derivative, mitomycin C, or paclitaxel, or to a primary or secondary amino group of amolecular targeted drug for cancer, such as gefitinib, erlotinib, lapatinib, or sunitinib, directly or through an amino acid-based spacer such as β-alanine, has excellent durability of antitumor effects and high safety, and the compound provides a superior therapeutic effect for malignant tumors at a small dose and a small number of times of administration compared to conventional antitumor agents. Thus, the inventors completed the present invention.

That is, the present invention provides the following [1] to [11].

[1] A compound of Formula (1), or a salt thereof:

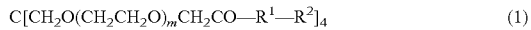

wherein $R^1$ represents a single bond, $-N(R^3)(CH_2)_{n1}CO-$, or $-N(R^4)(CH_2)_{n2}N(R^5)CO(CH_2)_{n3}CO-$, wherein $R^3$ represents a hydrogen atom or an alkyl group; $R^4$ and $R^5$, which are identical or different from each other, each represent a hydrogen atom or an alkyl group, or $R^4$ and $R^5$ are bonded together and represent an alkylene group having 1 to 4 carbon atoms; and n1, n2, and n3, which are identical or different from each other, each represent an integer of from 1 to 3;

$R^2$ represents a group of Formula (a), (b), (c), (d), (e), or (f):

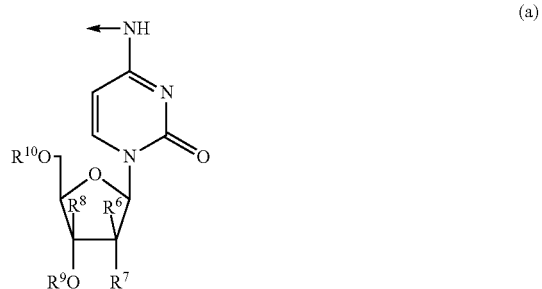

(a)

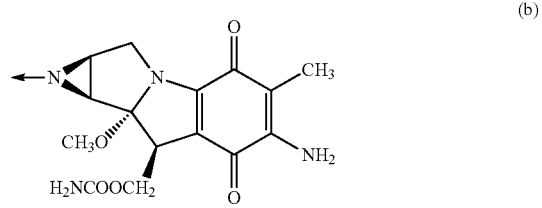

(b)

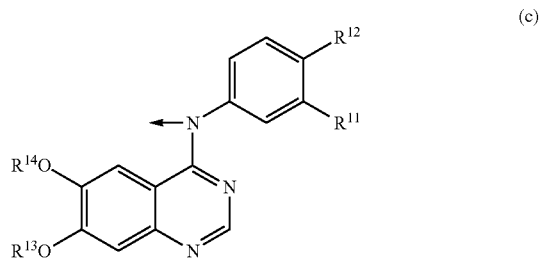

(c)

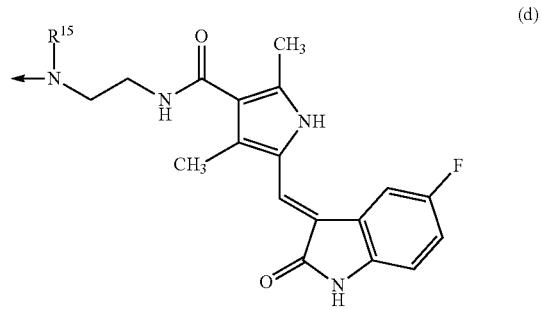

(d)

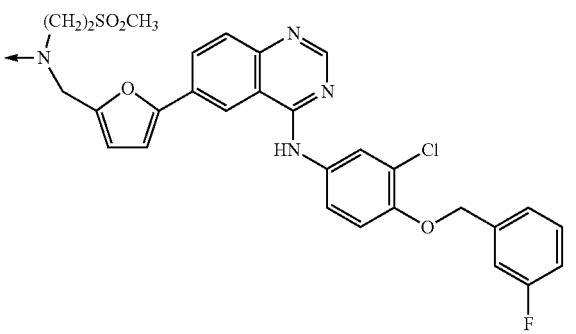

(e)

(f)

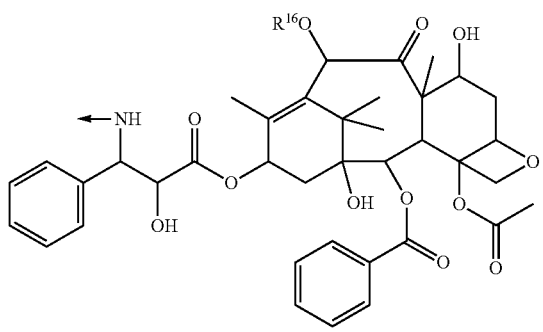

wherein R[6] represents a hydroxyl group, a cyano group, or a halogen atom; R[7] represents a hydrogen atom or a halogen atom; R[8] represents a hydrogen atom or an ethynyl group; R[9] and R[10], which are identical or different from each other, each represent a hydrogen atom or a trialkylsilyl group, or R[9] and R[10] are bonded together and represent a tetraalkylsiloxysilyl group; R[11] represents a halogen atom or an ethynyl group; R[12] represents a hydrogen atom or a halogen atom; R[13] represents an alkyl group or an alkoxyalkyl group; R[14] represents an alkoxyalkyl group or a morpholinoalkyl group; R[15] represents an alkyl group; and R[16] represents a hydrogen atom or an alkanoyl group;

m represents a number of from 10 to 1,000; and an arrow represents a bonding site.

[2] The compound according to [1] or a salt thereof, wherein R[2] represents a group of Formula (a) or (b).

[3] The compound according to [1] or [2], or a salt thereof, wherein R[2] represents a group of Formula (a).

[4] The compound according to any one of [1] to [3] or a salt thereof, wherein R[2] represents a group of Formula (a); R[6] represents a hydroxyl group, a cyano group or a halogen atom; R[7] represents a hydrogen atom or a halogen atom; R[8] represents a hydrogen atom or an ethynyl group; and R[9] and R[10] each represent a hydrogen atom.

[5] The compound according to any one of [1] to [4], or a salt thereof, wherein R[1] represents a single bond, —NH(CH$_2$)$_{n1}$CO—, —NH(CH$_2$)$_{n2}$NHCO(CH$_2$)$_{n3}$CO—, or the following formula:

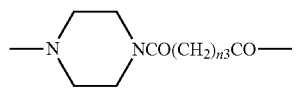

wherein n1, n2, and n3 respectively have the same meanings as defined above).

[6] A medicine including the compound represented by any one of [1] to [5], or a salt thereof.

[7] The medicine according to [6], wherein the medicine is a therapeutic agent for a malignant tumor.

[8] A pharmaceutical composition including the compound according to any one of [1] to [5], or a salt thereof, and a pharmaceutically acceptable salt.

[9] Use of the compound according to any one of [1] to [5], or a salt thereof, for the production of a therapeutic agent for a malignant tumor.

[10] The compound according to any one of [1] to [5], or a salt thereof, for the use in the treatment of a malignant tumor.

[11] A method for treating a malignant tumor, the method including administering an effective amount of the compound according to any one of [1] to [5], or a salt thereof.

ADVANTAGEOUS EFFECTS OF INVENTION

Since Compound (1) of the present invention has excellent anti-malignant tumor effects and has superior effect durability, Compound (1) exhibits excellent anti-malignant tumor activity at a small dose (as converted to the active substance of the original antitumor agent), a small number of times of administration, and a low frequency of administration compared to conventional antitumor agents, and also has reduced adverse effects. Therefore, when a treatment for a malignant tumor using Compound (1) of the present invention is employed, the burden of patients and the burden of physicians are both reduced, and excellent anti-malignant tumor effects are obtained.

DESCRIPTION OF EMBODIMENTS

Figure 1:
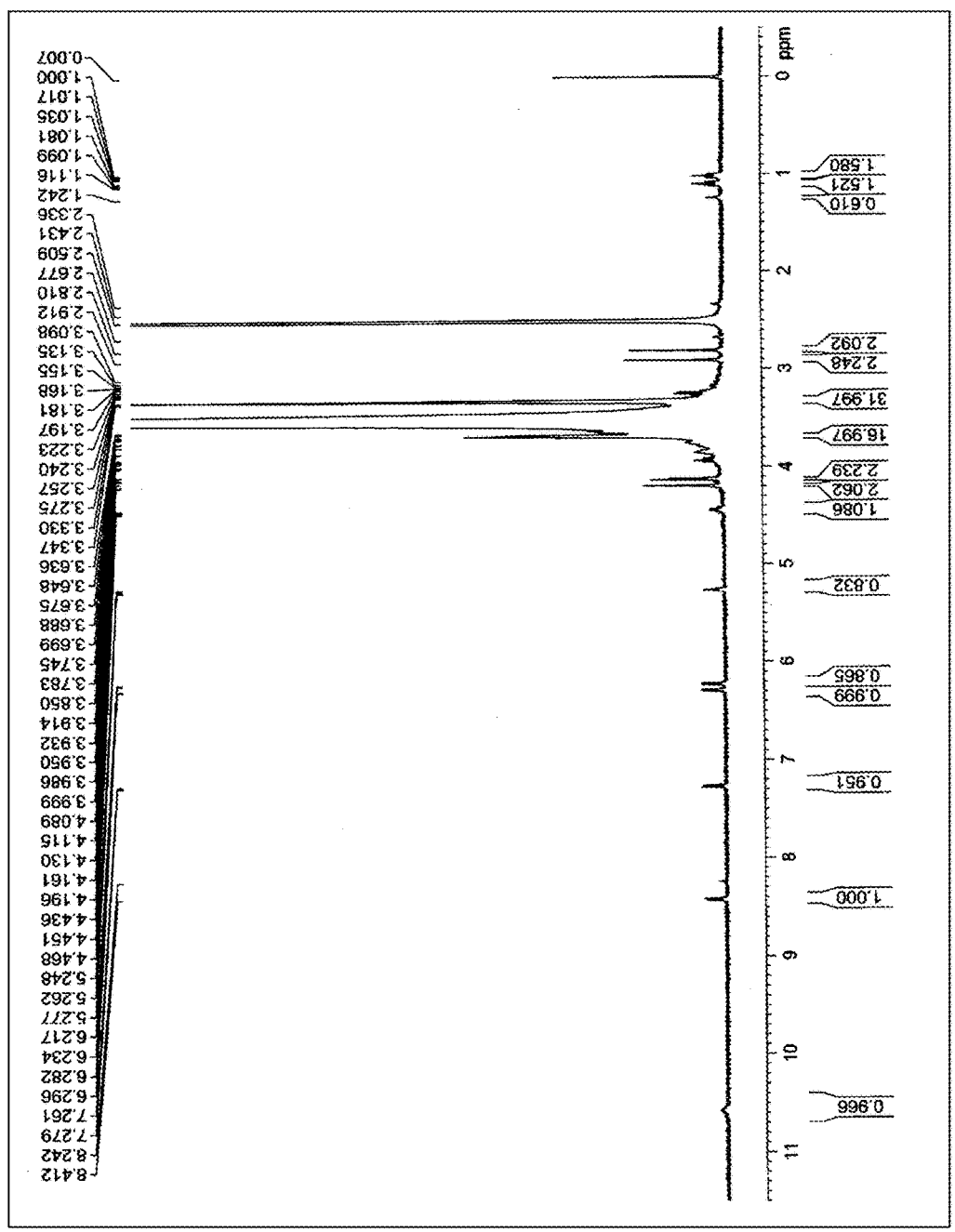
FIG. 1 illustrates an NMR spectrum chart of Compound (1a).

In Formula (1), R[1] represents a single bond, —N(R[3])(CH$_2$)$_{n1}$CO—, or —N(R[4]) (CH$_2$)$_{n2}$N(R[5])CO(CH$_2$)$_{n3}$CO—, wherein R[3] represents a hydrogen atom or an alkyl group; R[4] and R[5], which may be identical or different from each other, each represent a hydrogen atom or an alkyl group, or R[4] and R[5] are bonded together and represent an alkylene group having 1 to 4 carbon atoms; and n1, n2, and n3, which may be identical or different from each other, each represent an integer of from 1 to 3.

The group of $R^3$, $R^4$ or $R^5$ is preferably a hydrogen atom, and when the group is an alkyl group, the alkyl group may be a linear or branched alkyl group having 1 to 6 carbon atoms. Above all, a linear or branched alkyl group having 1 to 4 carbon atoms is preferred, and for example, a methyl group, an ethyl group, and an isopropyl group are more preferred.

The alkylene group having 1 to 4 carbon atoms that is formed by $R^4$ and $R^5$ together may be a methylene group, an ethylene group, a trimethylene group, or a tetramethylene group, and an ethylene group is more preferred.

$R^3$ is more preferably a hydrogen atom. Regarding $R^4$ and $R^5$, it is more preferable that both represent a hydrogen atom, or $R^4$ and $R^5$ form a $C_{1-3}$ alkylene group.

n1, n2 and n3 each represent an integer of 1, 2, or 3, and among these, 2 is more preferable.

More preferred examples of $R^1$ include a single bond, —NH(CH$_2$)$_{n1}$CO—, —NH(CH$_2$)$_{n2}$NHCO(CH$_2$)$_{n3}$CO—, and

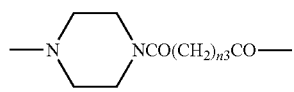

Even more preferred specific examples of $R^1$ include a single bond, —NHCH$_2$CH$_2$CO— and

$R^2$ represents a group of Formula (a), (b), (c), (d), (e), or (f):

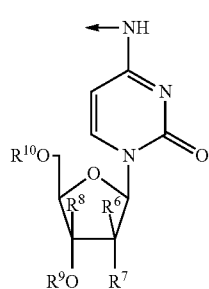

(a)

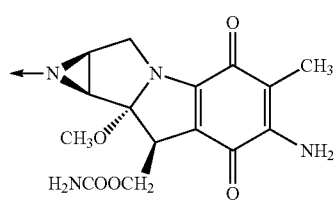

(b)

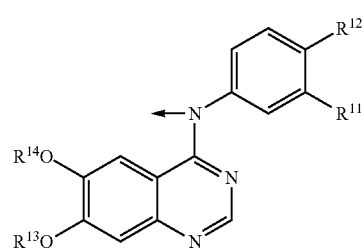

(c)

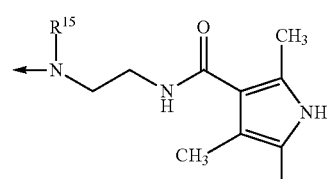

(d)

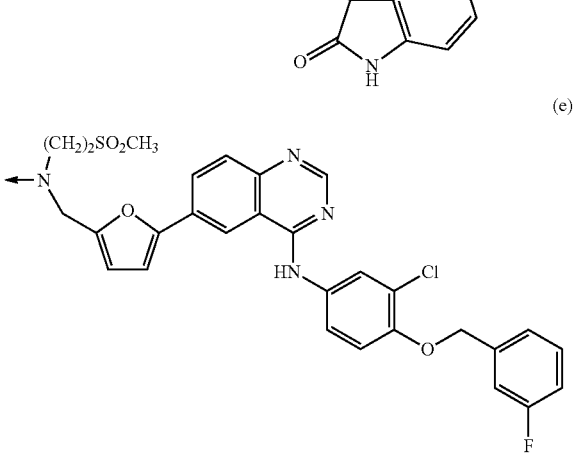

(e)

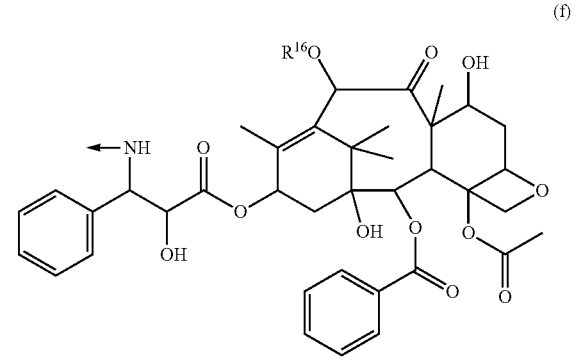

(f)

wherein $R^6$ represents a hydroxyl group, a cyano group, or a halogen atom; $R^7$ represents a hydrogen atom or a halogen atom; $R^8$ represents a hydrogen atom or an ethynyl group; $R^9$ and $R^{10}$, which are identical or different from each other, each represent a hydrogen atom or a trialkylsilyl group, or $R^9$ and $R^{10}$ are bonded together and represent a tetraalkyl-siloxysilyl group; $R^{11}$ represents a halogen atom or an ethynyl group; $R^{12}$ represents a hydrogen atom or a halogen atom; $R^{13}$ represents an alkyl group or an alkoxyalkyl group; $R^{14}$ represents an alkoxyalkyl group or a morpholinoalkyl group; $R^{15}$ represents an alkyl group; $R^{16}$ represents a hydrogen atom or an alkanoyl group; and an arrow represents a bonding site.

$R^6$ represents a hydroxyl group, a cyano group, or a halogen atom; however, a cyano group is particularly preferred. $R^7$ represents a hydrogen atom or a halogen atom. Here, the halogen atom is preferably a fluorine atom.

$R^8$ represents a hydrogen atom or an ethynyl group.

Examples of the trialkylsilyl group of $R^9$ or $R^{10}$ include a trimethylsilyl group, a triethylsilyl group, a triisopropylsilyl group, a dimethylbutylsilyl group, and a dimethylpentylsilyl group. The tetraalkylsiloxysilyl group formed by $R^9$ and $R^{10}$ together is preferably a group of the following Formula (g):

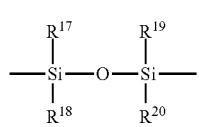

(g)

wherein $R^{17}$, $R^{18}$, $R^{19}$, and $R^{20}$ each represent an alkyl group, and for example, a methyl group, an ethyl group, an isopropyl group, a butyl group, and a pentyl group are preferred.

$R^{11}$ represents a halogen atom or an ethynyl group. $R^{12}$ represents a hydrogen atom or a halogen atom.

$R^{13}$ represents an alkyl group or an alkoxyalkyl group. Here, the alkyl group is preferably an alkyl group having 1 to 6 carbon atoms, and more preferably a methyl group. Regarding the alkoxyalkyl group, a $C_{1-6}$ alkoxy-$C_{1-6}$ alkyl group is preferred; for example, a methoxyethyl group, a methoxypropyl group, and an ethoxyethyl group are more preferred; and a methoxyethyl group is particularly preferred.

$R^{14}$ represents an alkoxyalkyl group or a morpholinoalkyl group. Here, the alkoxyalkyl group is preferably a $C_{1-6}$ alkoxy-$C_{1-6}$ alkyl group; more preferably a methoxyethyl group, a methoxypropyl group, or an ethoxyethyl group; and particularly preferably a methoxyethyl group. The morpholinoalkyl group is preferably a morpholino-$C_{1-4}$ alkyl group, and more preferably a morpholinopropyl group.

$R^{15}$ is preferably a $C_{1-6}$ alkyl group; and more preferably a methyl group, an ethyl group, a propyl group, or a butyl group.

$R^{16}$ is preferably a hydrogen atom or an alkanoyl group having 2 to 6 carbon atoms; and more preferably a hydrogen atom or an acetyl group.

The group of Formula (a), (b), (c), (d), (e), or (f) is a group derived from an anticancer agent. Formula (a) represents a group derived from an arabinofuranosylcytosine-based anticancer agent. Formula (b) represents a group derived from mitomycin C. Formula (c) represents a group derived from an EGFR tyrosine kinase inhibitor such as gefinitib or erlotinib. Formula (d) represents a group derived from a PDGFR tyrosine kinase inhibitor such as sunitinib. Formula (e) represents a group derived from an EGFR tyrosine kinase inhibitor such as lapatinib. Formula (f) represents a group derived from a taxane-based anticancer agent such as paclitaxel or docetaxel.

Preferred examples of the structure of Formula (a) include β-D-arabinofuranosylcytosine, 2'-cyano-2'-deoxy-β-D-arabinofuranosylcytosine, 2'-deoxy-2',2'-difluoro-β-D-arabinofuranosylcytosine, and 3'-ethynyl-β-D-arabinofuranosylcytosine.

Specific examples of the group of Formula (c) include a group of Formula (c1) and a group of Formula (c2):

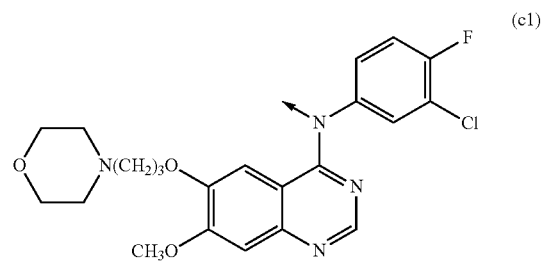

(c1)

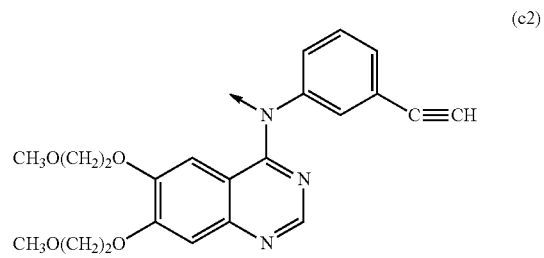

(c2)

Specific examples of the group of Formula (f) include a group of Formula (f1) and a group of Formula (f2):

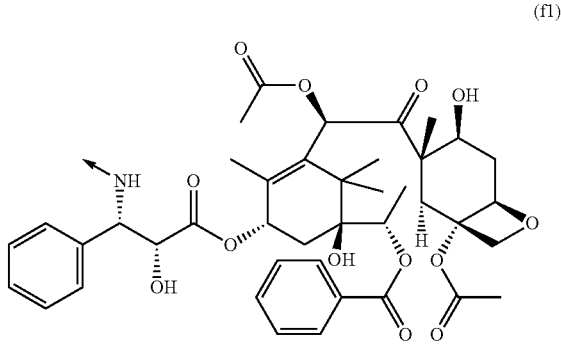

(f1)

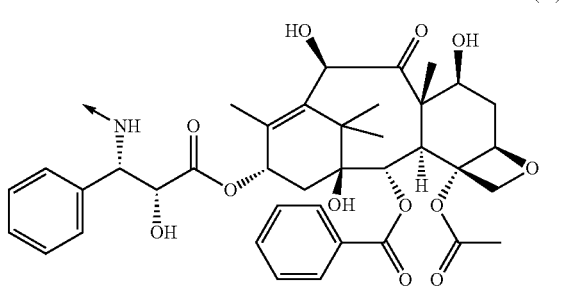

(f2)

m represents a number of from 10 to 1, 000. A more preferred value of m is from 100 to 500, and an even more preferred value of m is from 200 to 300. m represents a number originating from a polyethylene glycol group, and is usually an average value.

The salt of Compound (1) of the present invention is not particularly limited as long as it is a pharmaceutically acceptable salt, and examples thereof include inorganic acid salts such as hydrochloride, sulfate, and nitrate; and organic acid salts such as acetate, citrate, tartrate, oxalate, and malate. Since Compound (1) of the present invention or a salt thereof has an asymmetric carbon atom, there are steric isomers, and optically active substances thereof, enantiomers, and mixtures thereof are included.

Compound (1) of the present invention or a salt thereof can be produced by, for example, the following reaction scheme:

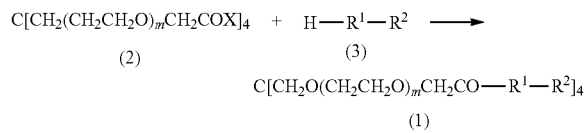

wherein X represents a hydroxyl group, a halogen atom, or an active ester residue of a carboxyl group; and $R^1$, $R^2$, and m respectively have the same meanings as described above.

That is, Compound (1) of the present invention or a salt thereof can be produced by bonding a carboxyl group of a tetracarboxylic acid derivative of Formula (2) to an amino group of a compound of Formula (3).

The tetracarboxylic acid derivative (2) is obtained by, for example, reacting pentaerythritol with ethylene oxide, subsequently carboxymethylating the reaction product, and further halogenating or active esterifying a carboxyl group. Examples of the halogen atom include a chlorine atom and a bromine atom. Examples of the active ester include succinimide and a mixed acid anhydride.

Among the derivatives of Compound (3), a compound in which $R^1$ represents —$N(R^3)(CH_2)_{n1}CO$— or —$N(R^4)(CH_2)_{n2}N(R^5)CO(CH_2)_{n3}CO$— is obtained by, for example, reacting a Compound (3) in which $R^1$ represents a single bond, with $HN(R^3)$ $(CH_2)_{n1}COY$ or $HN(R^4)$ $(CH_2)_{n2}N(R^5)CO(CH_2)_{n3}COY$. Here, $R^3$, $R^4$, $R^5$, n1, n2, and n3 respectively have the same meanings as described above; and Y represents a hydroxyl group, a halogen atom, or an active ester residue.

This reaction is a carboxylic acid amide-forming reaction, and can be carried out using a condensing agent such as HBTU or DCC in the presence of a base.

The reaction between the tetracarboxylic acid derivative (2) and the Compound (3) is a carboxylic acid amide-forming reaction, and can be carried out under conventional amidation reaction conditions. For example, the reaction can be carried out under the conditions of from 0° C. to 150° C. in the presence of an amine such as triethylamine or N,N-dimethylaniline.

After completion of the reaction, the target material can be purified and isolated by means of washing, recrystallization, and various chromatographic means.

Compound (1) of the present invention or a salt thereof has excellent anti-malignant tumor activity and has reduced adverse effects such as body weight reduction, and excellent anti-malignant tumor effects are obtained without requiring sustained infusion that lasts several hours or longer. Therefore, the Compound (1) or a salt thereof is useful as an excellent therapeutic agent for a malignant tumor with reduced burden for patients and physicians.

Compound (1) of the present invention or a salt thereof is such that there is only an amide bond as the bond between PEG and the anticancer agent, and thus the compound or the salt can avoid rapid decomposition by lyases in blood, such as esterases or carboxylases. Unlike the liposomes or polymer micelles of microparticulate preparations that are likely to become the object of attack by phagocytes, the Compound (1) or the salt has a very small molecular size per se, is not likely to be attacked by phagocytes due to the characteristics of PEG, and is very stable in blood. Furthermore, since the renal excretion rate is also very low due to the large molecular weight, targeting to a tumor is highly of. As a result, the dosage can be extremely lowered compared to the case of conventional low molecular weight anticancer agents that have been administered by methods such as intravenous administration or oral administration. In addition, not only the number of administrations can be reduced to a large extent, but also the duration of administration per time can be in around 30 minutes for an anticancer agent that has been conventionally relied on long-time sustained infusion.

Examples of the malignant tumor that becomes an object of application of the Compound (1) of the present invention or a salt thereof include head and neck cancer, esophageal cancer, gastric cancer, colon cancer, rectal cancer, liver cancer, gall bladder and bile duct cancer, pancreatic cancer, lung cancer, breast cancer, ovarian cancer, cervical cancer, uterine cancer, renal cancer, urinary bladder cancer, prostate cancer, testicular tumor, bone and soft tissue sarcomas, leukemia, malignant lymphoma, multiple myeloma, skin cancer, brain tumor, and mesothelial tumor.

On the occasion of using Compound (1) of the present invention or a salt thereof, a pharmaceutical composition of various forms can be produced by mixing the compound or the salt with a pharmaceutically acceptable carrier as necessary. Examples of the form of the pharmaceutical composition include a peroral agent, an injectable preparation, a suppository, a patch, and an ointment; however, it is preferable to prepare the compound or the salt as an injectable preparation.

Regarding the pharmaceutically acceptable carrier, various organic or inorganic carrier materials that are conventionally used as preparation materials are used, and the carrier is incorporated as an excipient, a binder, a disintegrant, a lubricating agent, or a colorant for solid preparations; and as a solvent, a dissolution aid, a suspending agent, an isotonic agent, a buffer agent, or a soothing agent for liquid preparations Furthermore, preparation additives such as an antiseptic agent, an antioxidant, a colorant, a sweetening agent, and a stabilizer can also be used as necessary.

When an oral solid preparation is produced, for example, an excipient, or an excipient, a binder, a disintegrant, a lubricating agent, a colorant, and a flavoring agent/corrigent are added to the Compound (1) of the present invention, and then for example, tablets, coated tablets, a granular preparation, a powder, and capsules can be produced by conventional methods.

When an injectable preparation is produced, for example, a pH adjusting agent, a buffer agent, a stabilizer, an isotonic agent, and a local anesthetic agent are added to the Compound (1) of the present invention, and a subcutaneous injectable preparation, an intramuscular injectable preparation, and an intravenous injectable preparation can be produced by conventional methods.

When the medicine of the present invention is used for the treatment of a malignant tumor in the blood system, it is preferable that the medicine is administered by means of intravenous administration within one hour, or by means of intravenous drip infusion within several hours after diluting the medicine with physiological saline or a glucose infusion solution.

EXAMPLES

Hereinafter, the present invention will be specifically described by way of Examples and Test Examples; however, these are described only for illustrative purposes, and are not intended to limit the scope of the present invention.

Example 1

Under a nitrogen atmosphere, 5.0 mol of 1-(2'-cyano-2'-deoxy-β-D-arabinofuranosyl)cytosine hydrochloride, 10.0 mol of triethylamine, and 8 mol of dimethylformamide were added to a reaction vessel, and 1.0 mol of tetra(succinimidylcarboxymethyl polyethylene glycol) pentaerythritol was added thereto. The mixture was heated to 100° C. and reacted with stirring for 3 hours. The reaction mixture was cooled to 20° C. to 25° C., and then the reaction mixture was introduced into 100 mL of methyl tert-butyl ether and stirred for one hour. The raw materials were separated by filtration. The residue was repeatedly subjected to an operation of adding ethanol at from 50° C. to 60°, stirring, subsequently cooling to 20±5° C., stirring for 16 hours, and washing with methyl tert-butyl ether, and the ethanol solution was cooled. Thus, Compound (1a) (m =230 on average) was obtained as a white powder (yield 88%). Melting point: 54° C. The NMR spectrum chart of Compound (1a) is presented in FIG. 1.

C[CH₂O(CH₂CH₂O)ₘCH₂CONH]₄  (1a)

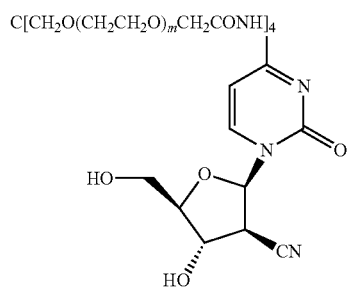

Example 2

(1) 1 mol of 1-(2'-cyano-2'-deoxy-β-D-arabinofuranosyl)cytosine hydrochloride and 100 mL of pyridine were introduced into a reaction vessel under a nitrogen atmosphere, and 1.2 mol of tetraisopropyldisiloxane dichloride was added dropwise thereto at from 20° C. to 25° C. The mixture was heated to 45±5° C. and stirred for 2 hours. Hexane was added thereto at from 20° C. to 25° C., and the product was isolated as a solid. The product was introduced into water at from 20° C. to 25° C., and the mixture was stirred for 1 hour and 30 minutes. After the mixture was filtered, the residue was washed with water and hexane, and was dried to solid by evaporation. Thus, Compound (3a) was obtained.

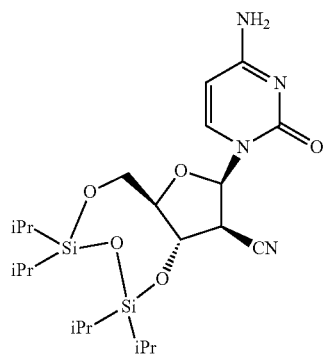

(2) 1.2 mol of N-t-butoxycarbonylalanine, 1.5 mol of HBTU, 2.0 mol of triethylamine, and 300 mL of dichloromethane were introduced into a reaction vessel under a nitrogen atmosphere, and the mixture was stirred for one hour at from 20° C. to 25° C. 1 mol of Compound (3a) was added thereto at from 20° C. to 25° C., and the mixture was heated to 35±5° C. and stirred for 16 hours. A saturated aqueous solution of NaHCO₃ was added thereto, and an organic phase was separated. The organic phase was washed respectively with a saturated aqueous solution of NaHCO₃, saturated NH₄Cl, and physiological saline, and the organic phase was dried over anhydrous Na₂SO₄. After filtration, the filtrate was concentrated under reduced pressure and was subjected to silica gel column chromatography (eluted with ethyl acetate). Thus, Compound (3b) was obtained (yield 77%).

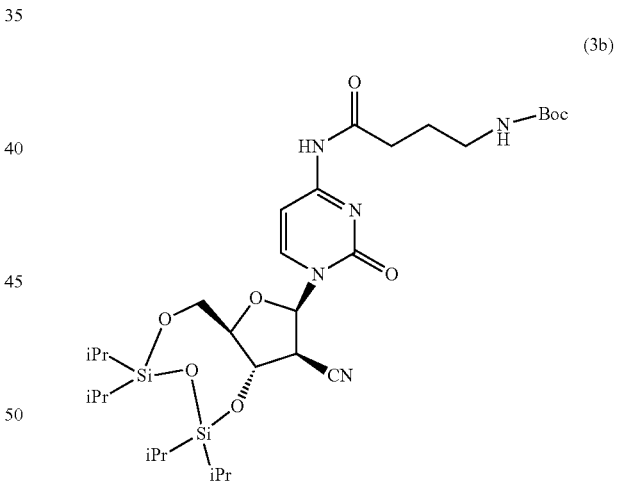

(3) 1 mol of Compound (3b), 2 mol of acetic acid, and 200 mL of tetrahydrofuran were introduced into a reaction vessel under a nitrogen atmosphere, the mixture was cooled to 0±5° C., and then 1.5 mol of tetra-n-butylammonium fluoride (TBAF) was added thereto at 0±5° C. The mixture was allowed to react for one hour, and then the solvent was distilled off.

Under a nitrogen atmosphere, the reaction mixture described above and 300 mL of ethyl acetate were introduced into a reaction vessel, and 2 M HCl/ethyl acetate was added thereto at 25±5° C. The starting materials rapidly dissolved in the concentrated HCl/ethyl acetate solution, and after 5 minutes, the intended product began to be separated as a solid fraction. The mixture was stirred for one hour, filtered, and then washed with ethyl acetate. Thus, Compound (3c) was obtained.

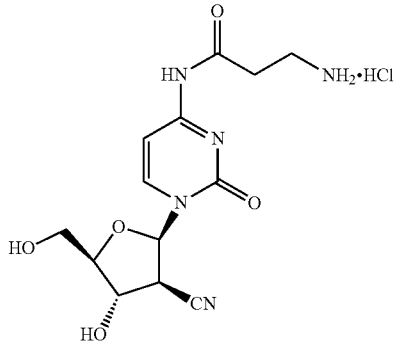
(3c)

Figure 2:
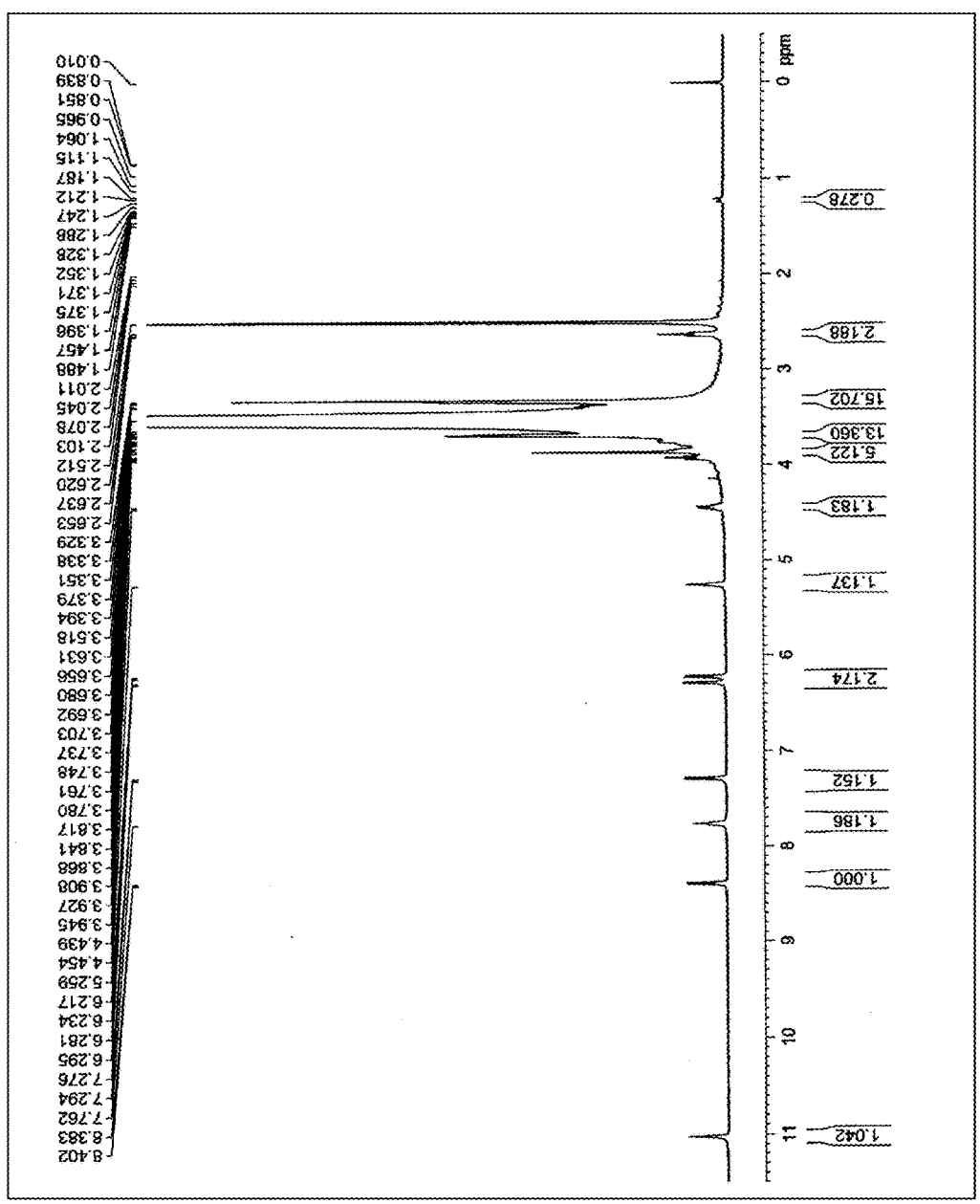
FIG. 2 illustrates an NMR spectrum chart of Compound (1b).

(4) Compound (3c) was reacted with tetra(succinimidylcarboxymethyl polyethylene glycol) pentaerythritol ether in the same manner as in Example 1, and target Compound (1b) (m=230 on average) was obtained as a white powder (yield 83%). The NMR spectrum chart of Compound (1b) is presented in FIG. 2.

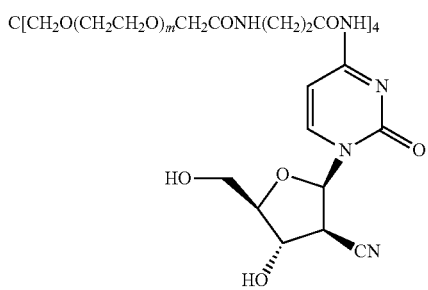
(1b)
C[CH$_2$O(CH$_2$CH$_2$O)$_m$CH$_2$CONH(CH$_2$)$_2$CONH]$_4$

Example 3

(1) 1 mol of Compound (3a) obtained in Example 2 (1), 4 mol of succinic anhydride, and 50 mL of pyridine were introduced into a reaction vessel under a nitrogen atmosphere, and the mixture was heated to 40±5° C. and stirred for 2 hours. The reaction mixture was added to a mixture of water and ethyl acetate, the pH of the mixture was adjusted to 5 using 1 M hydrochloric acid, and the mixture was stirred for 30 minutes at 30±5° C. An organic phase was separated, the aqueous phase was extracted three times with ethyl acetate, and the organic phases thus extracted were combined and washed with physiological saline. The organic phase was dried over anhydrous Na$_2$SO$_4$ and filtered, and then the filtrate was concentrated under reduced pressure and then dried. Thus, Compound (3d) was obtained.

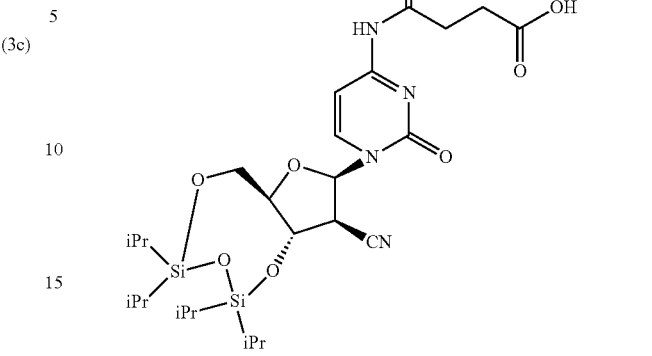
(3d)

(2) 1 mol of Compound (3d), 2 mol of HBTU, 4 mol of triethylamine, and 100 mL of dimethylformamide were introduced into a reaction vessel under a nitrogen atmosphere, and the mixture was stirred for 5 minutes at 30±5° C. 4 mol of piperidine was added thereto, and the mixture was stirred for one hour at 30±5° C. Ethyl acetate and water were added thereto, an organic phase was separated, and the organic phase was washed two times with physiological saline and dried over anhydrous Na SO$_4$. After filtration, the filtrate was concentrated under reduced pressure, was subjected to silica gel column chromatography, and was eluted with dichloromethane/MeOH. The eluted fraction was dried to solid under reduced pressure, and Compound (3e) was obtained.

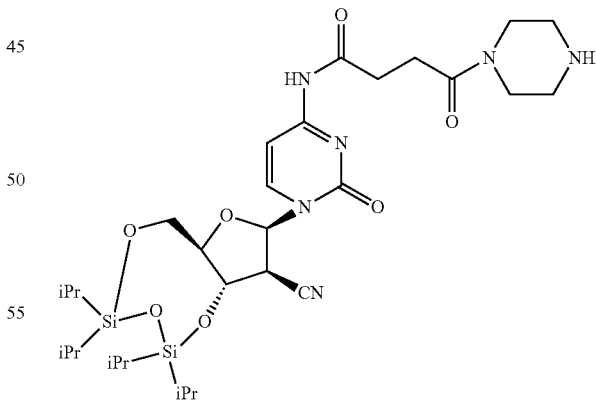
(3e)

Figure 3:
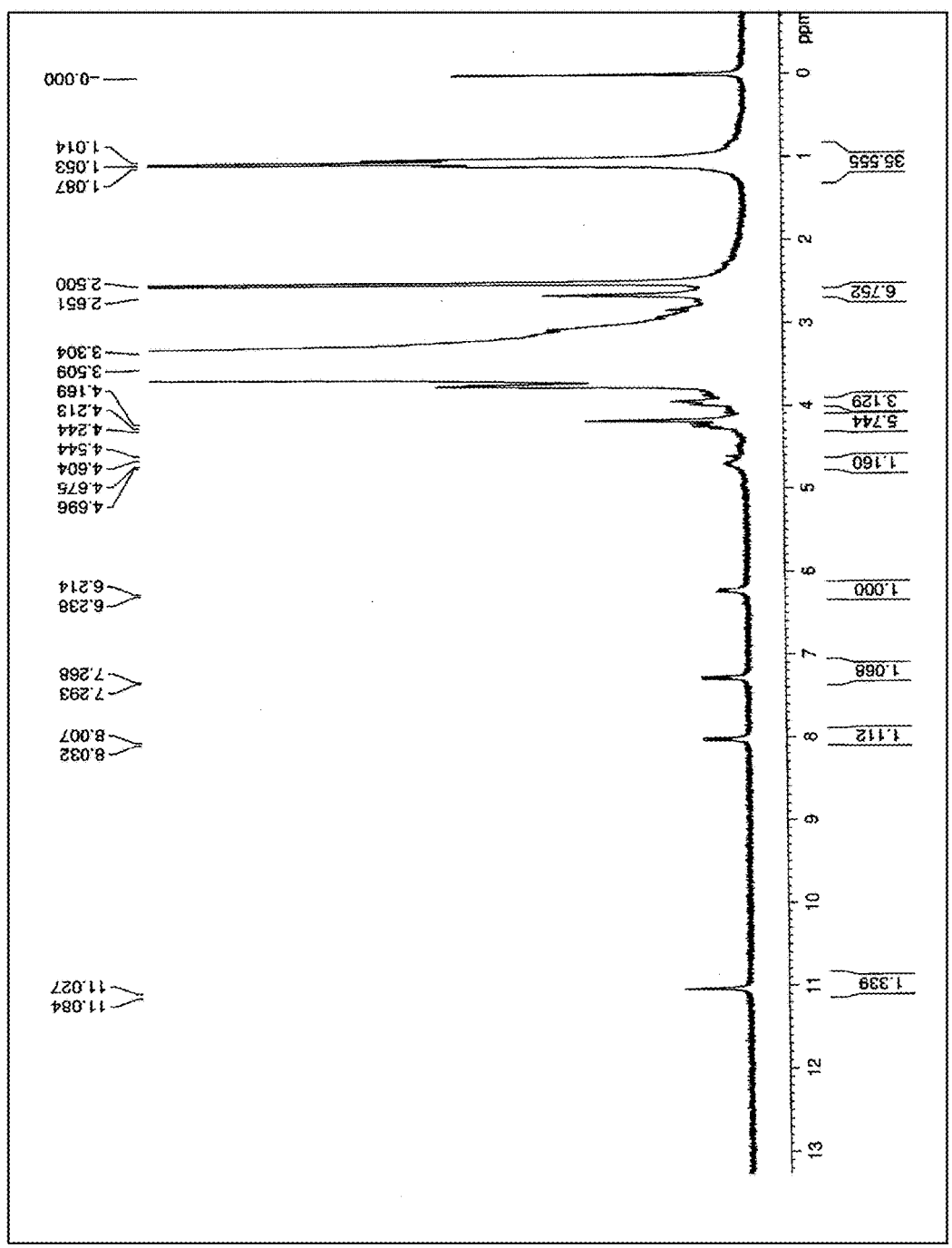
FIG. 3 illustrates an NMR spectrum chart of Compound (1c).

(3) Compound (3e) was reacted with tetra(succinimidylcarboxymethyl polyethylene glycol) pentaerythritol ether in the same manner as in Example 1, and target Compound (1c) (m=230 on average) was obtained as a white powder (yield 94%). The NMR spectrum chart of Compound (1c) is presented in FIG. 3.

(1c)

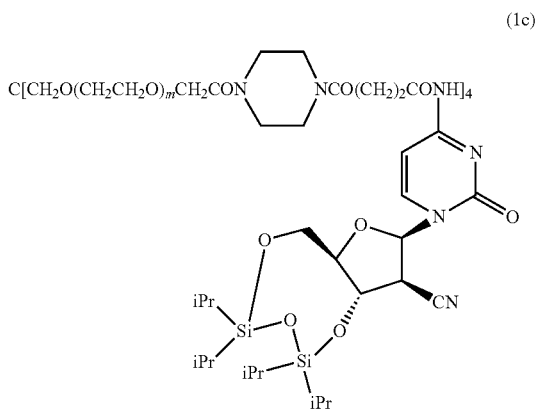

Example 4

(1) 1 mol of Compound (3e) of Example 3(2), 2.3 mol of acetic acid, and 50 mL of dimethylformamide were introduced into a reaction vessel under a nitrogen atmosphere, and the mixture was cooled to 0±5° C. 1. 6 mol of tetra-n-butylammonium fluoride (TBAF) was added thereto at 0±5° C., and the mixture was stirred for one hour. Thus, Compound (3g) was produced.

(3g)

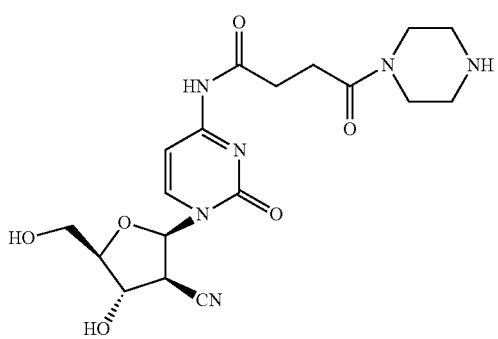

Figure 4:
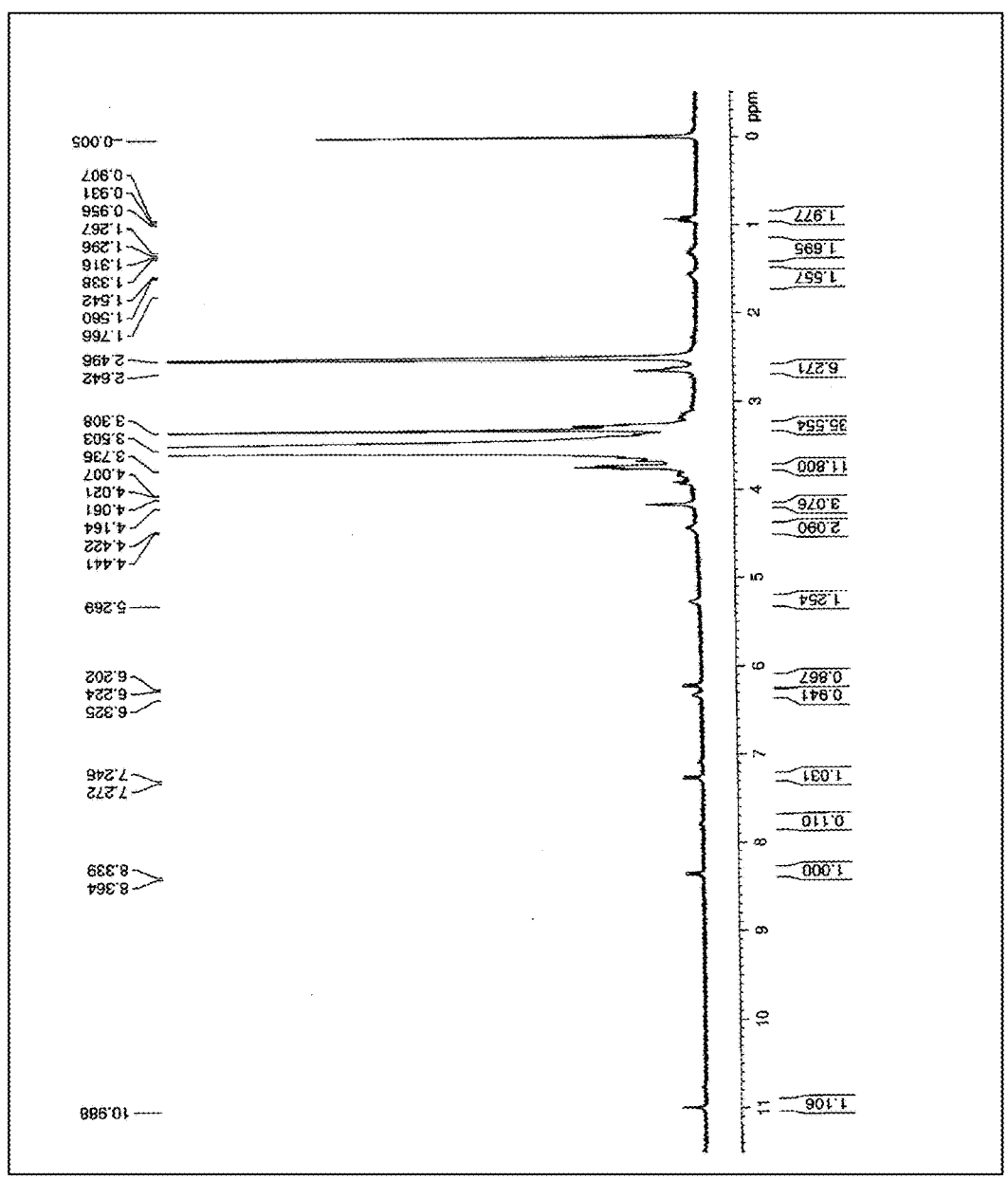
FIG. 4 illustrates an NMR spectrum chart of Compound (1d).

(2) Compound (3g) was reacted with tetra(succinimidyl-carboxymethyl polyethylene glycol) pentaerythritol ether in the same manner as in Example 1, and Compound (1d) (m=230 on average) was obtained. The NMR spectrum chart of Compound (1d) is presented in FIG. 4.

(1d)

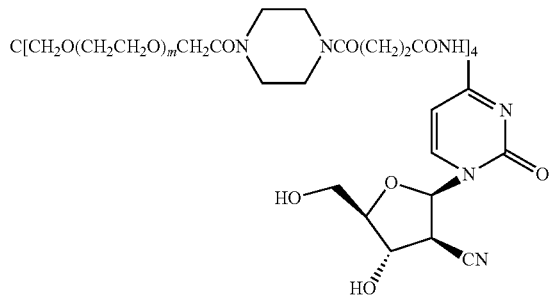

Example 5

Figure 5:
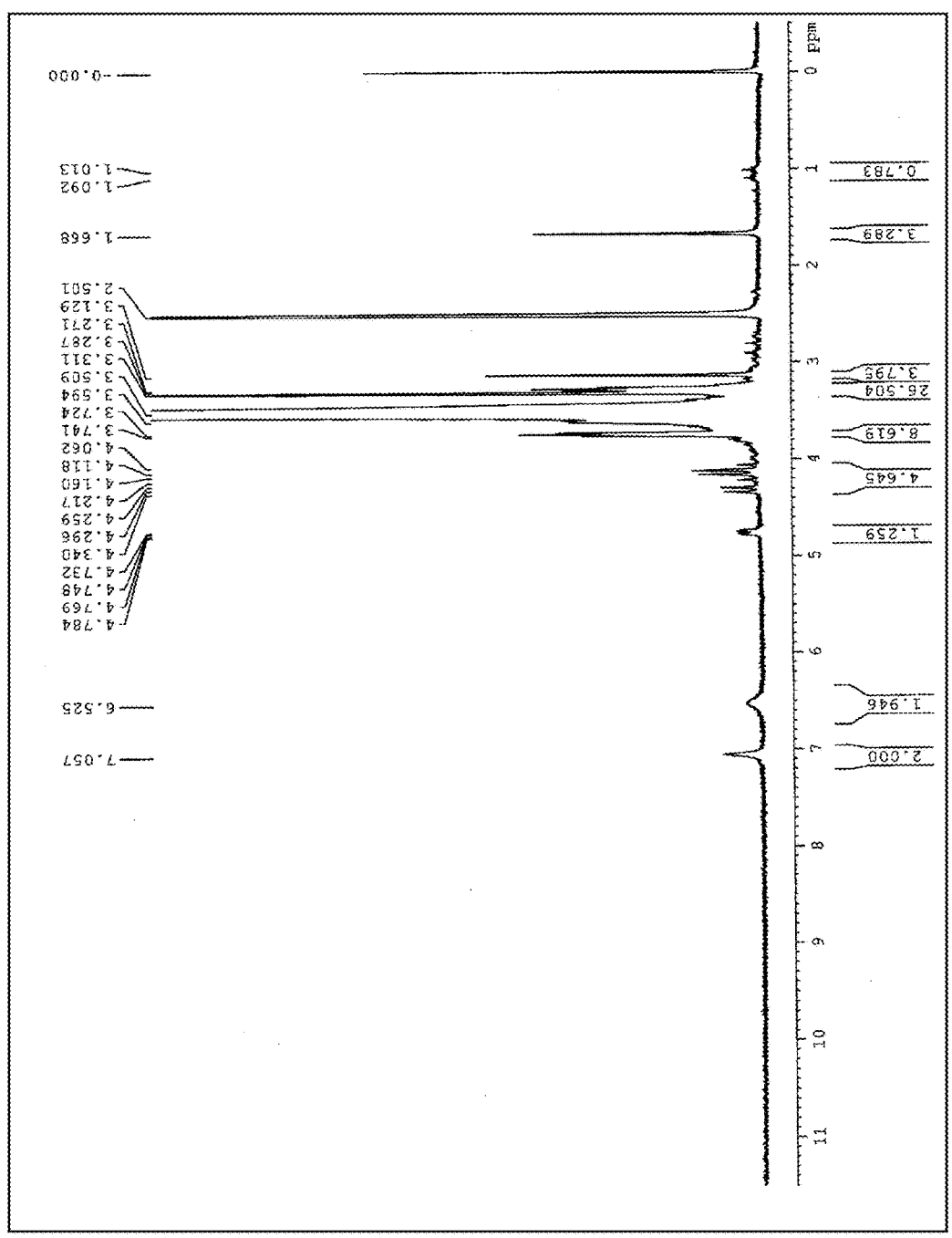
FIG. 5 illustrates an NMR spectrum chart of Compound (1e).

1.0 mol of tetra(carboxymethyl polyethylene glycol) pentaerythritol, 4.8 mol of mitomycin C, 5.0 mol of HBTU, 8 mol of triethylamine, and 300 mL of dimethylformamide were added to a reaction vessel under a nitrogen atmosphere, and the mixture was allowed to react for 3 hours at 40 ±5° C. The mixture was cooled to 20° C. to 25° C., and then was treated in the same manner as in Example 1. Thus, Compound (1e) was obtained as a white powder (m=230 on average) (yield 91.4%). The NMR spectrum chart of Compound (1e) is presented in FIG. 5.

(1e)

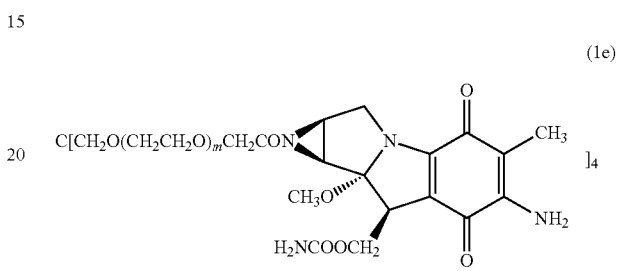

Example 6

(1) Compound (3h) was obtained in the same manner as in Example 3(1), using mitomycin C instead of Compound (3a).

(3h)

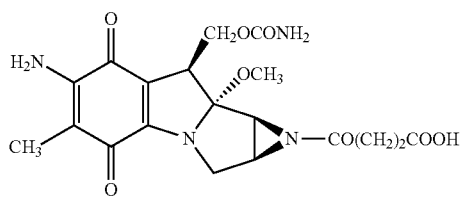

(2) Compound (3i) was obtained in the same manner as in Example 4(1), using Compound (3h) instead of Compound (3e).

(3i)

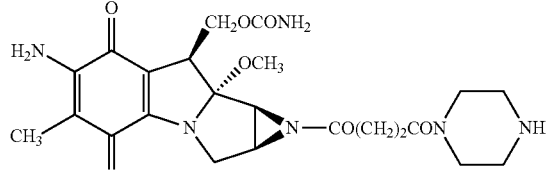

Figure 6:
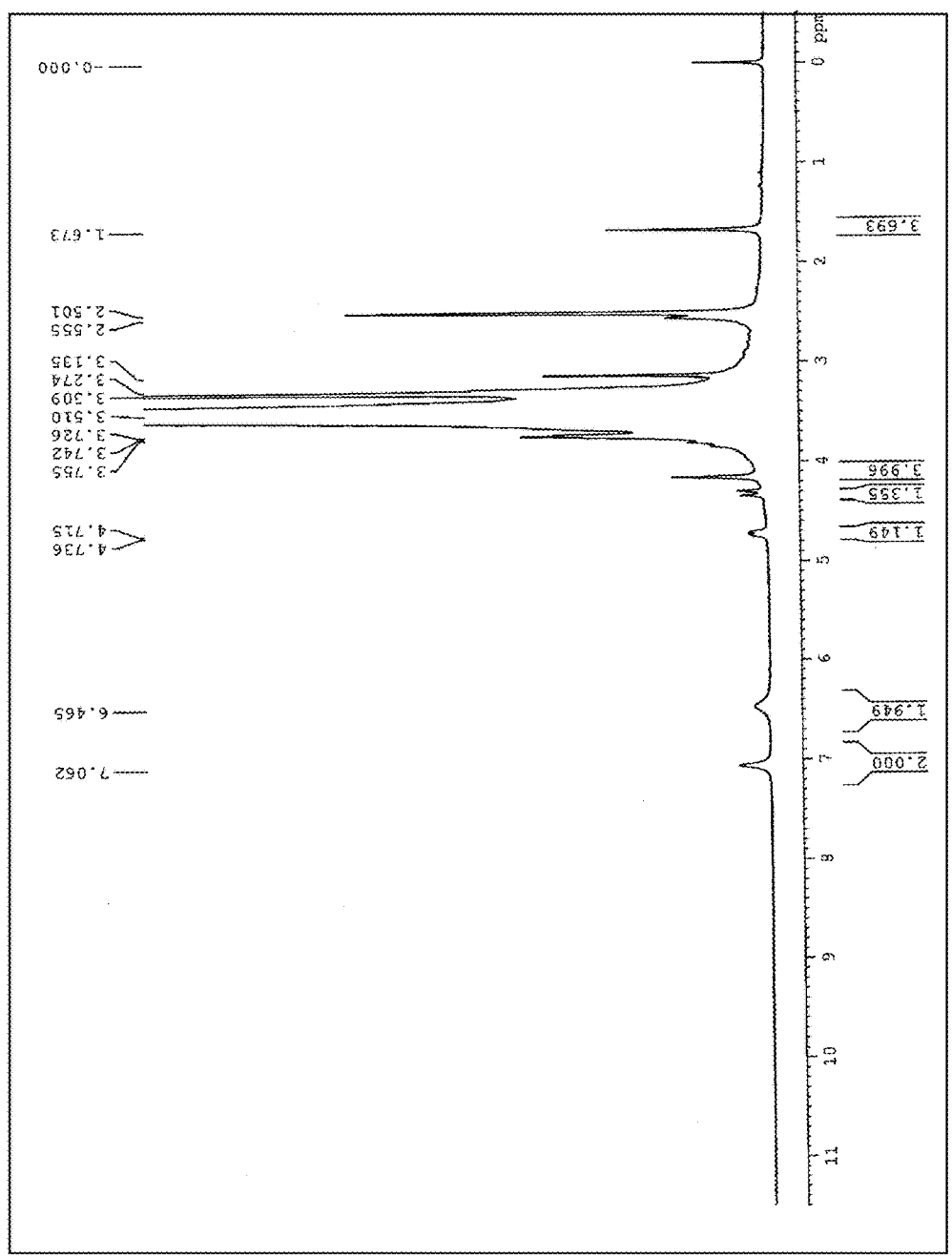
FIG. 6 illustrates an NMR spectrum chart of Compound (1f).

(3) Compound (1f) was obtained (m=230 on average) in the same manner as in Example 4 (2), using Compound (3i) instead of Compound (3g). The NMR spectrum chart of Compound (1f) is presented in FIG. 6.

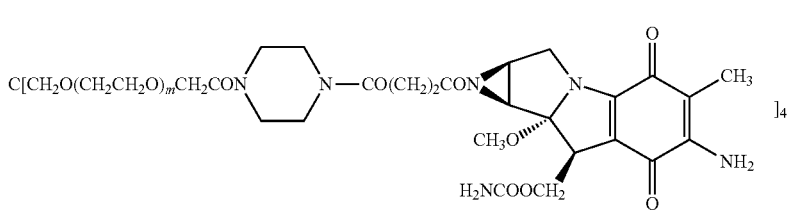

(1f)

Example 7

Figure 7:
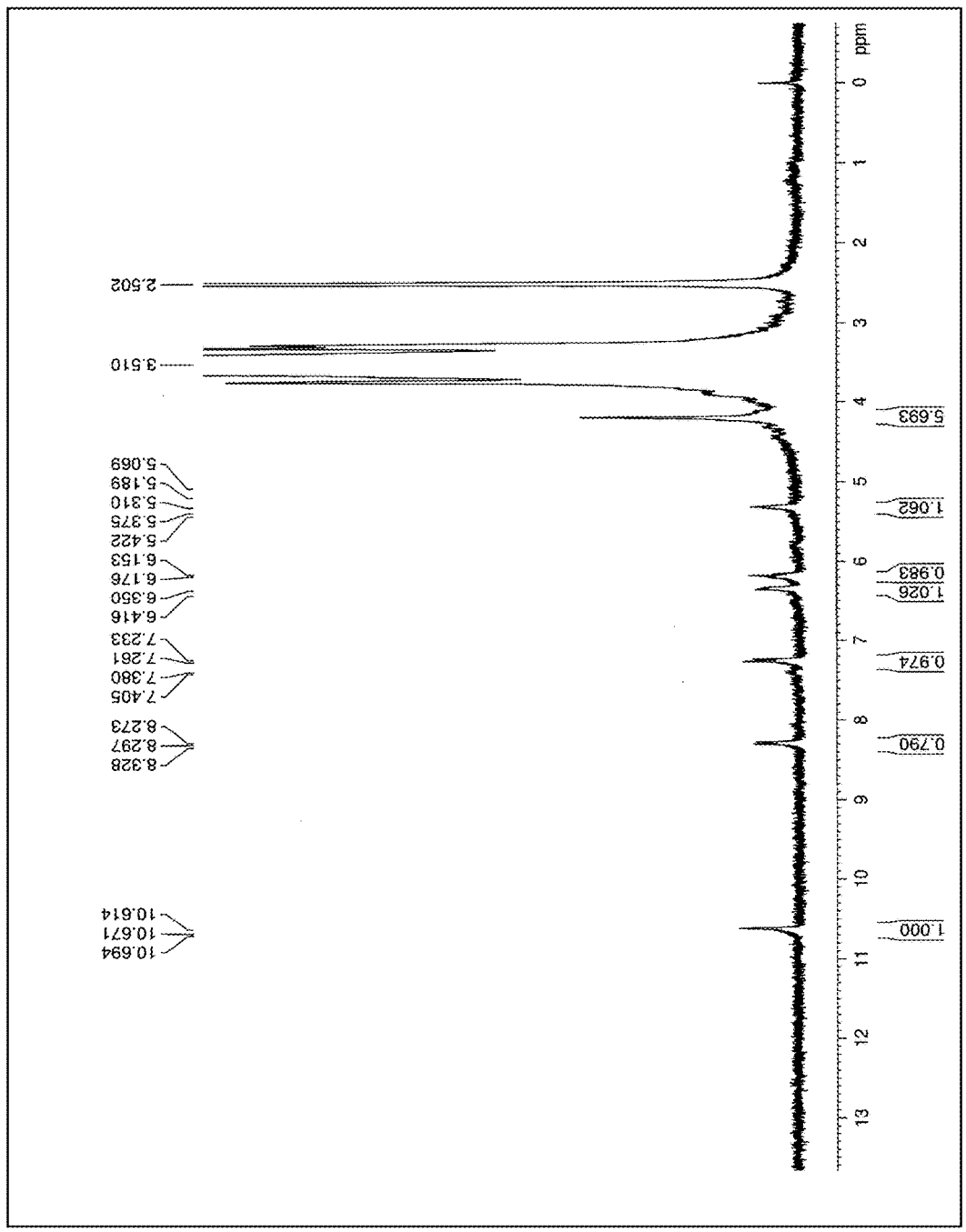
FIG. 7 illustrates an NMR spectrum chart of Compound (1g).

Compound (1g) (m=230 on average) was obtained as a white powder (yield 82.3%) in the same manner as in Example 1, using gemcitabine and tetra(succinimidylcarboxymethyl polyethylene glycol) pentaerythritol. Melting point 57° C. The $^1$H-NMR spectrum chart is presented in FIG. 7.

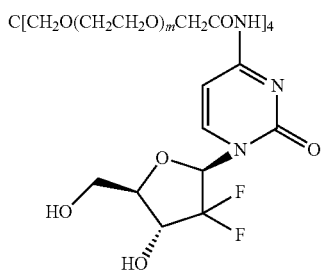

(1g)

Example 8

Figure 8:
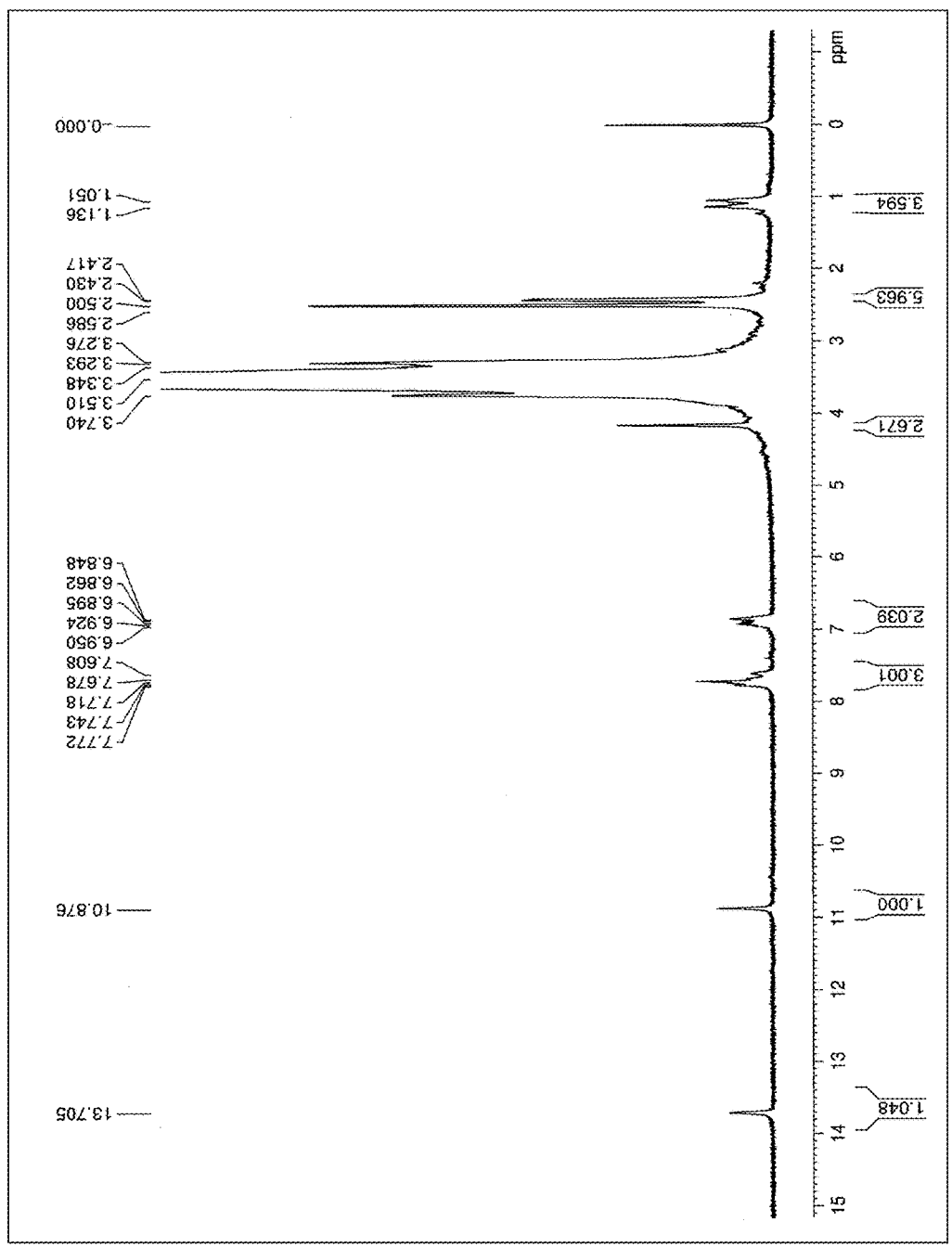
FIG. 8 illustrates an NMR spectrum chart of Compound (1h).

Compound (1h) (m=230 on average) was obtained as a yellow powder (yield 87%) in the same manner as in Example 1, using a de-ethylated form of sunitinib and tetra(succinimidylcarboxymethyl polyethylene glycol) pentaerythritol. Melting point 55° C. The $^1$H-NMR spectrum chart is presented in FIG. 8.

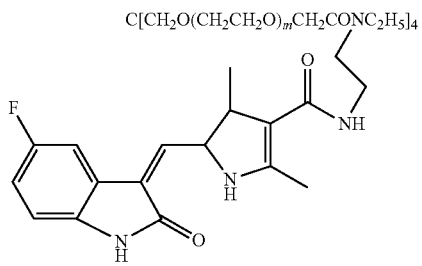

(1h)

Example 9

Figure 9:
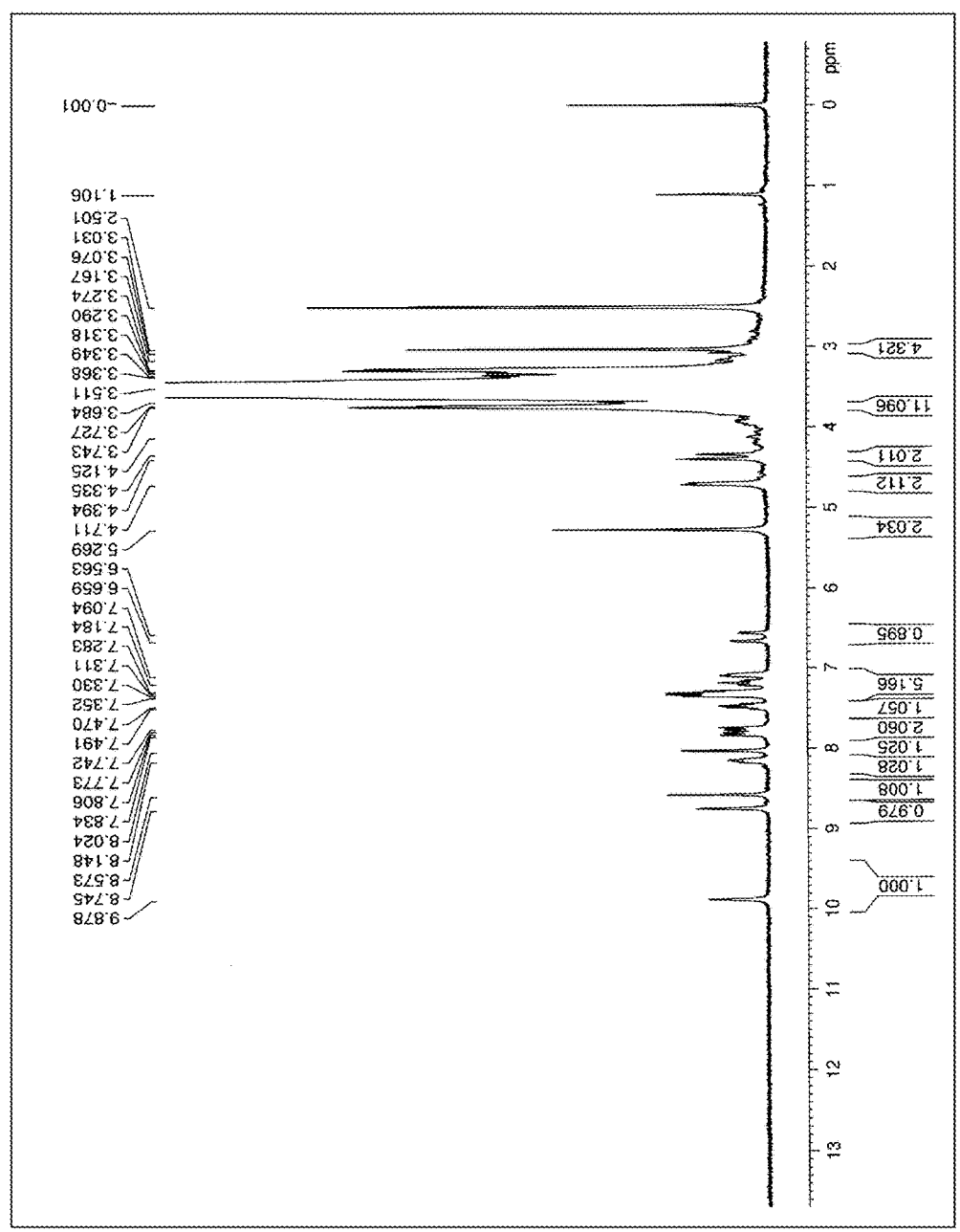
FIG. 9 illustrates an NMR spectrum chart of Compound (1i).

Compound (1i) was obtained as a white powder (yield 87.8%) in the same manner as in Example 4, using lapatinib, tetra (carboxymethyl polyethylene glycol) pentaerythritol, and HBTU. Melting point 56° C. The $^1$H-NMR spectrum chart is presented in FIG. 9.

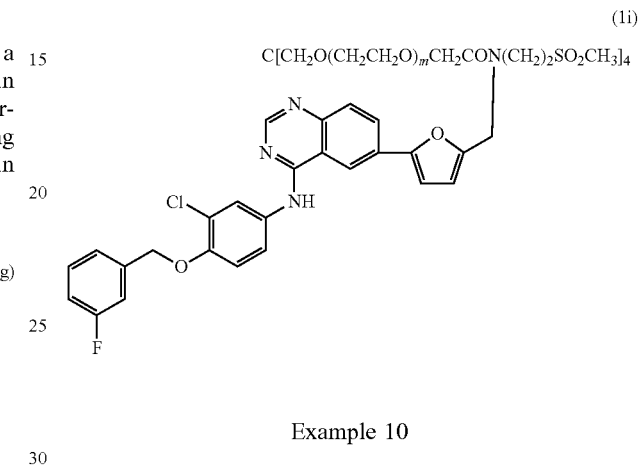

(1i)

Example 10

(1) Paclitaxel was reacted with trifluoroacetic acid, and thus a tert-butoxycarbonyl group of paclitaxel was detached.

Figure 10:
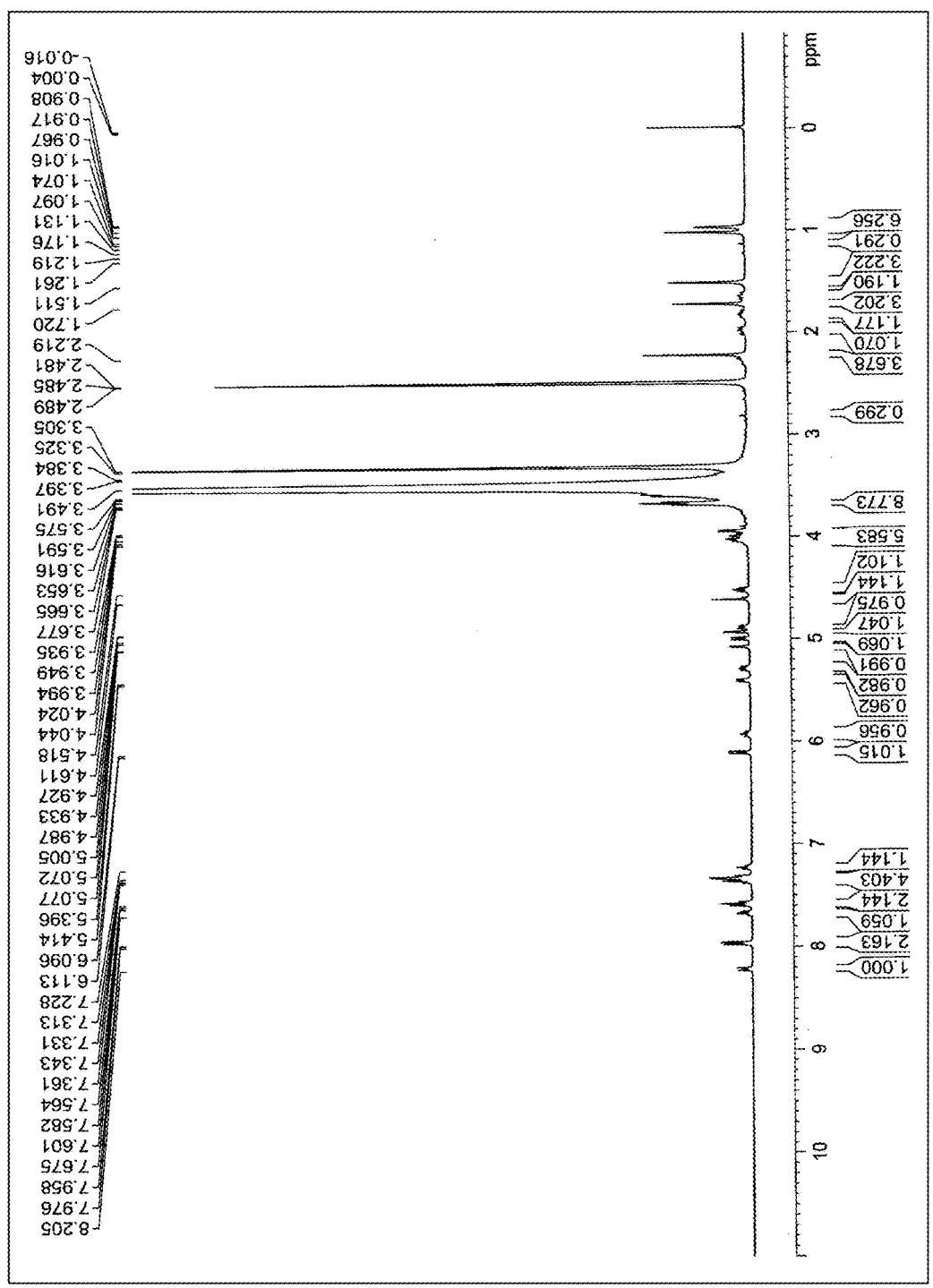
FIG. 10 illustrates an NMR spectrum chart of Compound (1j).

(2) Compound (1j) was obtained (yield 84.2%) in the same manner as in Example 1, using the t-butoxycarbonyl-detached form of paclitaxel and tetra(succinimidylcarboxymethyl polyethylene glycol) pentaerythritol. The $^1$H-NMR chart is presented in FIG. 10.

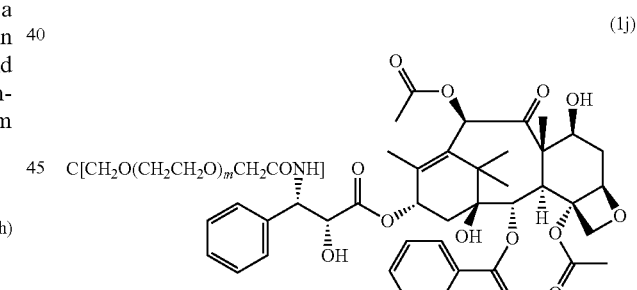

(1j)

Test Example 1

$5 \times 10^6$ cells of pancreatic cancer cells were transplanted into the right abdomen of a BALB/c nude mouse, and after 7 days, at the time point at which the average tumor size reached 100 mm$^3$, drug administration was initiated. Up to 29 days from the time of drug administration, the body weight of the mouse and the tumor volume were measured. The results are presented in FIG. 11, FIG. 12, and Table 1. Subcutaneous continuous infusion of 1-(2'-cyano-2'-deoxy-β-D-arabinofuranosyl)cytosine hydrochloride (DFP-10917) at a dose of 4.5 mg/kg/day was continuously performed for two weeks using a micropump embedded in the body of the mouse. In contrast, Compound (1a) was intravenously administered once a week at a dose of 100 mg/kg, 200 mg/kg, or 300 mg/kg. The dosage of this Compound (1a) is administration once a week at a dose of 2.4 mg/kg, 4.8 mg/kg, or 7.2 mg/kg, as converted to DFP-10197. For the control, a buffer solution (pH=5.0) of sodium acetate was administered.

Figure 11:
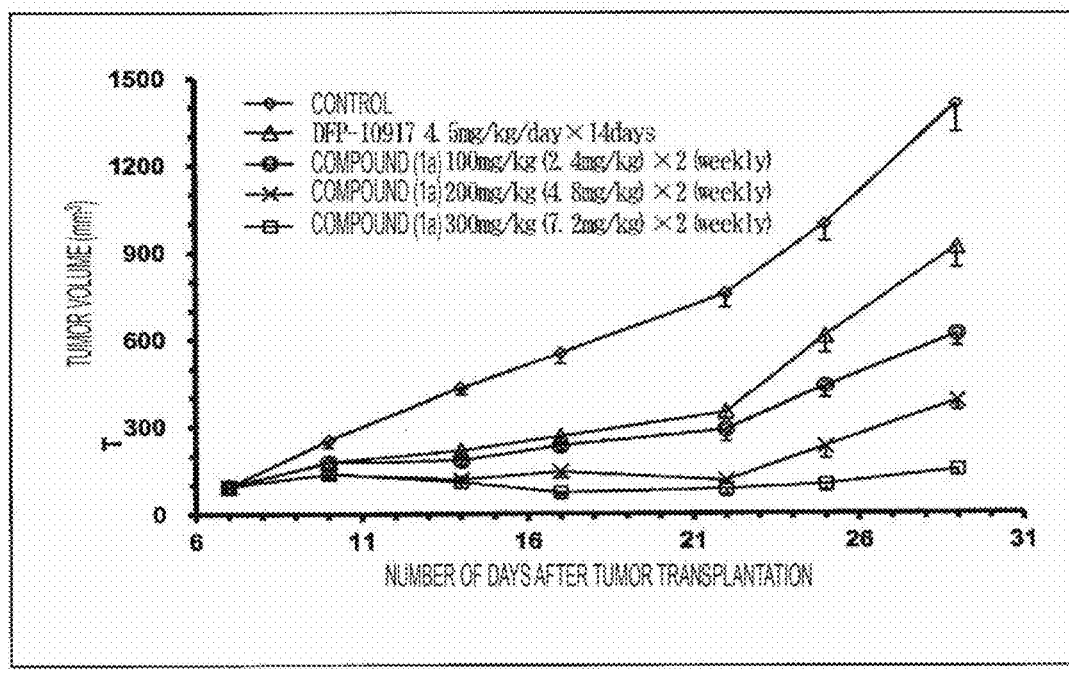
FIG. 11 illustrates changes in tumor volume after tumor transplantation. The value in the parentheses for the dose represents the dose as converted to DFP-10917.
Figure 12:
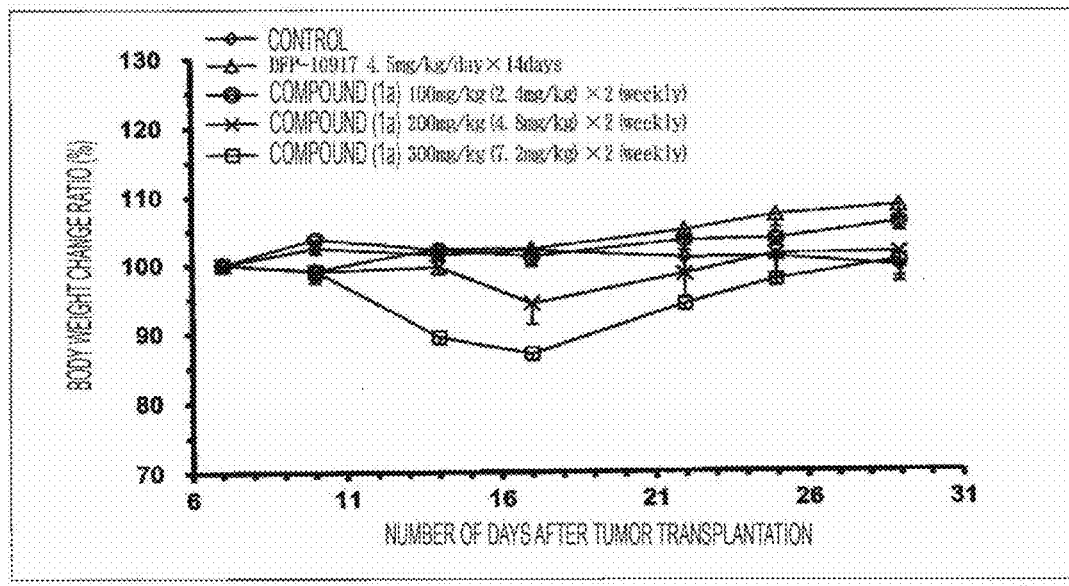
FIG. 12 illustrates a body weight change ratio (%) after tumor transplantation. The value in the parentheses for the dose represents the dose as converted to DFP-10917.

From FIG. 11 and FIG. 12, it was confirmed that Compound (1a) exhibits an excellent therapeutic effect for a tumor by intravenous administration once a week, almost without reducing the body weight.

TABLE 1

| Drug | Tumor Volume$^a$ (D 29, mm$^3$) | TGl$^b$ (D 29, %) | P value$^c$ |
|---|---|---|---|
| G1: Control | 1,409 ± 15 | — | — |
| G2: DFP-10917 4.5 mg/kg/day × 14 days | 917 ± 72 | 37.7 | 0.01 |
| G3: Compound (1a) 100 mg/kg × 2 (2.4 mg/kg × 2) | 617 ± 40 | 58.5 | <0.001 |
| G4: Compound (1a) 200 mg/kg × 2 (4.8 mg/kg × 2) | 386 ± 31 | 73.7 | <0.001 |
| G5: Compound (1a) 300 mg/kg × 2 (7.2 mg/kg × 2) | 150 ± 21 | 89.1 | — |

Note:
$^a$Mean ± SEM;
$^b$TGI: tumor growth inhibition.
$^c$vs. vehicle control.

P value: G2 vs. G3=0.027, G2 vs. G4=0.001, G3 vs. G4=0.004. The value in the parentheses of the dose indicates the dose as converted to DFP-10917.

Test Example 2

The antitumor activity of mitomycin C and Compound (1e) was investigated in the same manner as in Test Example 1. Mitomycin C (MMC) was intravenously administered once a week at a dose of 3 mg/kg/day. In contrast, Compound (1e) was intravenously administered once a week at a dose of 25 mg/kg, 50 mg/kg, 100 mg/kg, or 200 mg/kg. The dose of this Compound (1e) was administration once a week at a dose of 0.8 mg/kg, 1.7 mg/kg, 3.3 mg/kg, or 6.7 mg/kg, as converted to MMC.

Figure 13:
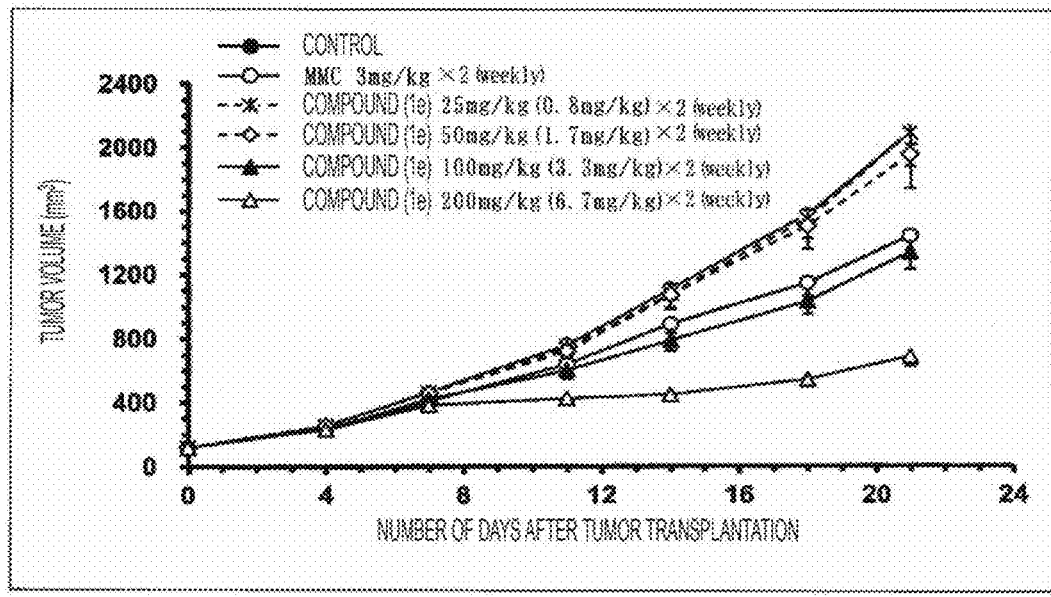
FIG. 13 illustrates changes in tumor volume after tumor transplantation. The value in the parentheses for the dose represents the dose as converted to MMC.
Figure 14:
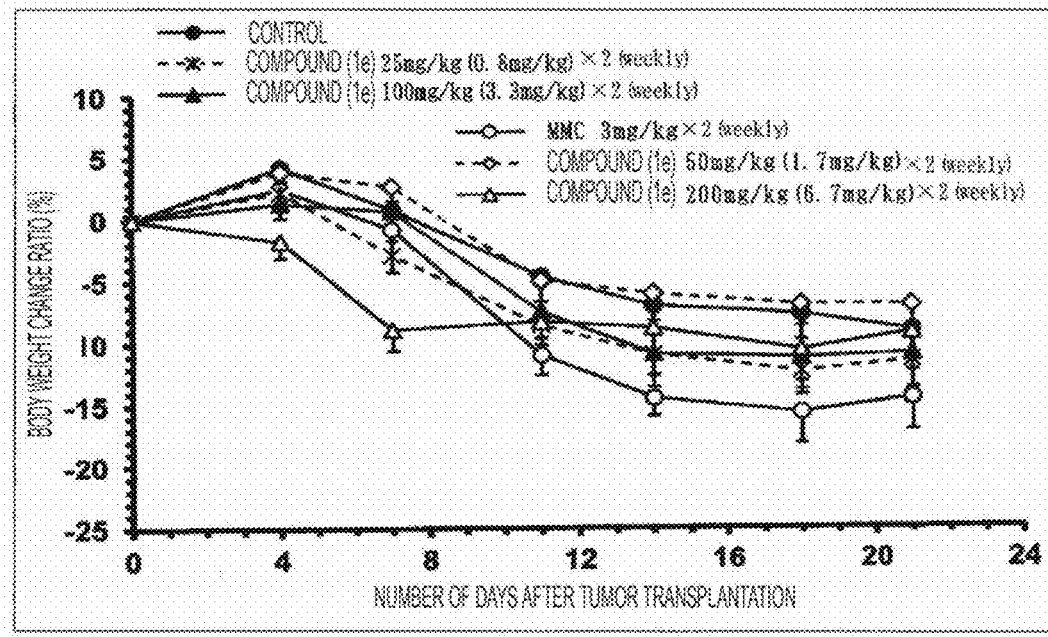
FIG. 14 illustrates a body weight change ratio (%) after tumor transplantation. The value in the parentheses for the dose represents the dose as converted tc-MMC.

From FIG. 13 and FIG. 14, it was confirmed that Compound (1e) exhibits an excellent therapeutic effect for a tumor by intravenous administration once a week, almost without reducing the body weight.

Test Example 3

5×10$^6$ cells of human lung cancer cell A549 were transplanted into the right abdomen of a BALE/c nude mouse, and after 14 days, at the time at which the average tumor size reached 127 mm$^3$, drug administration was initiated. Compound (1a) was intravenously administered once a week at a dose of 200 mg/kg (the amount as converted to DFP-10917 was 4.8 mg/kg), and pemetrexed, which is a standard drug for lung cancer, was intraperitoneally administered once a week at a dose of 300 mg/kg. For the control, physiological saline was intravenously administered once a week. The observation was made for two weeks (administered two times in total).

As a result, Compound (1a), which was administered at a dose of 4.8 mg/kg as converted to DFP-10917, exhibited a therapeutic effect for a tumor equivalent to that of the group administered with 300 mg/kg of pemetrexed.

TABLE 2

| Drug | Dose (mg/kg) | Total dosage (mg/kg) | Tumor Volume | TGI (tumor growth inhibition) | P value |
|---|---|---|---|---|---|
| Control | — | — | 1191 ± 103 | — | — |
| Pemetrexed | 300 | 600 | 818 ± 44 | 30 | 0.017 |
| Compound (1a) | 200 (4.8*) | 400 (9.6*) | 892 ± 57 | 24 | 0.066 |

*Dose as converted to DFP-10917

Test Example 4

1×10$^7$ cells of human breast cancer cell BT474 were transplanted into the right abdomen of a BALB/c nude mouse, and drugs were administered in the same manner as in Test Example 3. DFP-10917 and Compound (1a) were intravenously administered once a week, two times in total. For the control, physiological saline was administered once a week.

As a result, as shown in (Table 3), Compound (1a) exhibited an antitumor effect equivalent to that of gemcitabine, despite that Compound (1a) was administered at a dose of 17.6/200 as converted to DFP-10917, relative to the dose of DFP-10917 itself.

TABLE 3

| Drug | Dose (mg/kg) | Total dosage (mg/kg) | Tumor Volume | TGI (tumor growth inhibition) | P value |
|---|---|---|---|---|---|
| Control | — | — | 918 ± 141 | — | — |
| Gemcitabine | 100 | 200 | 525 ± 95 | 43 | 0.007 |
| Compound (1a) | 300 (8.8*) | 600 (17.6*) | 523 ± 95 | 43 | 0.006 |

*Dose as converted to DFP-10917

Test Example 5

5×10$^6$ cells of human pancreatic cancer cell Panc-1 were transplanted into the right abdomen of a BALB/c nude mouse, and drugs were administered in the same manner as in Test Example 3. Compound (1g) was intravenously administered once a week, two times in total, or twice a week. Gemcitabine was administered such that 100 mg/kg was administered in four divided portions over 3 days, and this intravenous administration was repeated four times in total. For the control, physiological saline was administered once a week.

As the results are presented in (Table 4), Compound (1g) exhibited an antitumor effect that was about ½ of the effect of gemcitabine, despite that Compound (1g) was administered at a dose of from 1/35 to 1/40 as converted to gemcitabine, relative to the dose of gemcitabine itself.

TABLE 4

| Drug and dose | Dose (mg/kg) | Total dosage (mg/kg) | Tumor Volume | TGI (tumor growth inhibition) | P value |
|---|---|---|---|---|---|
| Control | — | — | 1017 ± 20 | — | — |
| Gemcitabine | 100 | 400 | 370 ± 37 | 63.6 | <0.001 |
| Compound (1g) | 200 (5.8*) | 400 (11.7*) | 705 ± 66 | 30.7 | 0.005 |
| Compound (1g) | 300 (8.8*) | 300 (8.8*) | 689 ± 73 | 32.3 | 0.009 |

*Dose as converted to gemcitabine

Test Example 5

Human lung cancer cell A549 cells were transplanted into the right abdomen of a BALB/c nude mouse, and after 11 days, at the time point at which the average tumor size reached 200 mm³, drug administration was initiated. The dosage schedule is presented in Table 5 and Table 6.

Figure 15:
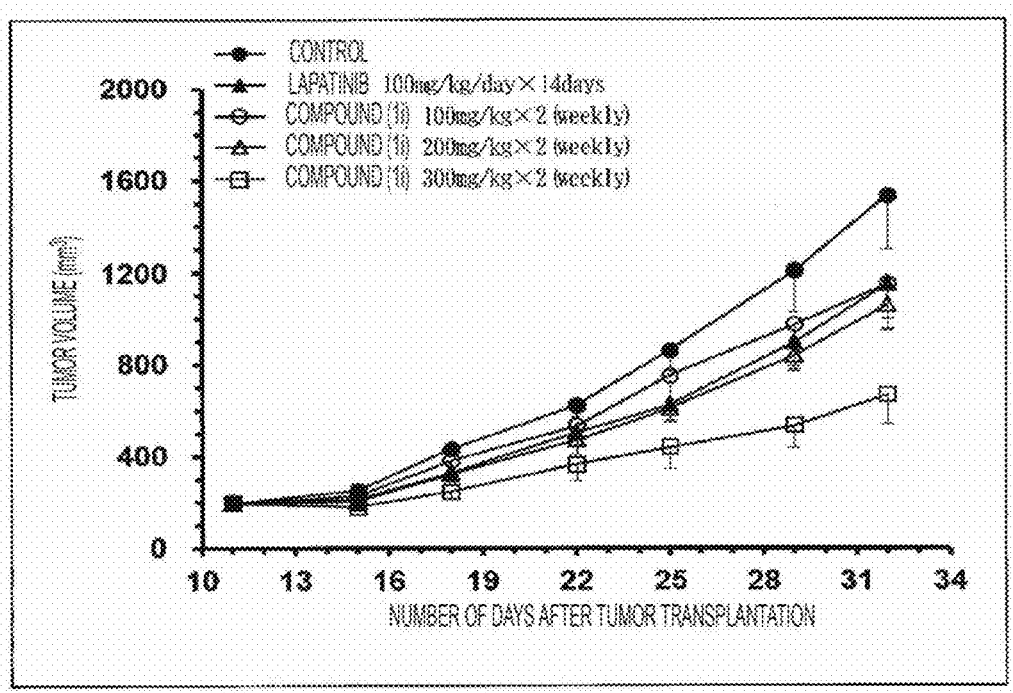
FIG. 15 represents changes in tumor volume after tumor transplantation.
Figure 16:
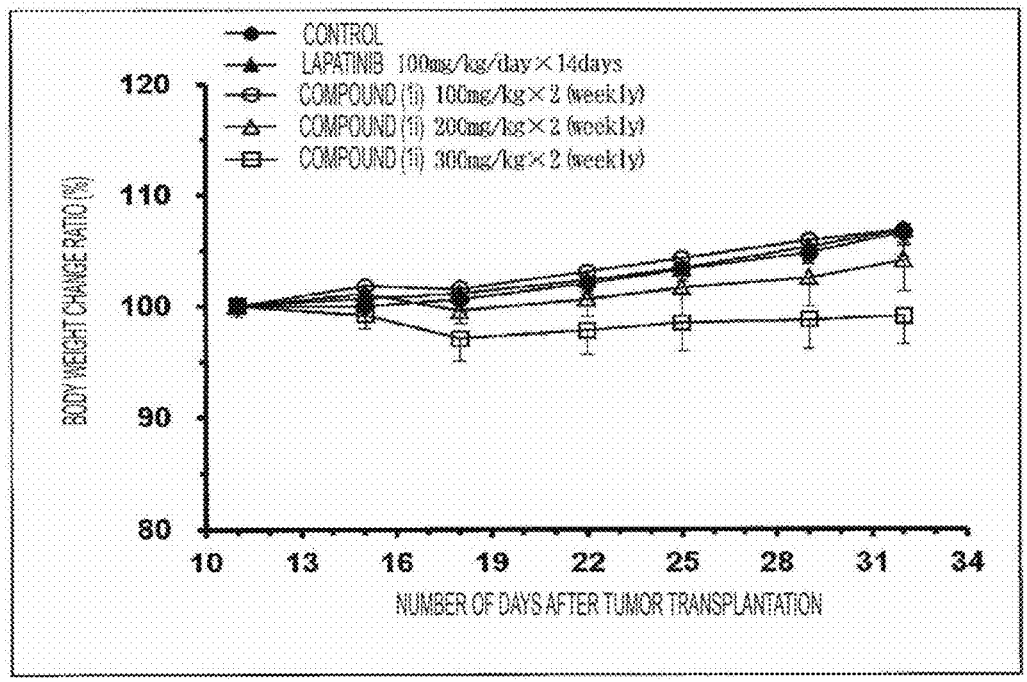
FIG. 16 represents a body weight change ratio (%) after tumor transplantation.

The results are presented in Table 5, Table 6, FIG. 15, and FIG. 16.

TABLE 5

| Drug and dose | Dosage schedule | Tumor Volume$^a$ (D 29, mm³) | TGl$^b$ (D 29, %) | P value$^c$ |
|---|---|---|---|---|
| Control | — | 1207 ± 180 | — | — |
| De-ethylated form of sunitinib (50 mg/kg) | po, once a day, for 2 weeks | 687 ± 103 | 43.1 | 0.004 |
| Compound (1h) (100 mg/kg) (4 mg/kg*) | iv, once a week, for 2 weeks | 817 ± 100 | 32.3 | 0.024 |
| Compound (1h) (200 mg/kg) (8 mg/kg*) | iv, once a week, for 2 weeks | 701 ± 77 | 41.9 | 0.005 |

*Dose as converted to sunitinib

TABLE 6

| Drug and dose | Dosage schedule | Tumor Volume$^a$ (D 29, mm³) | TGl$^b$ (D 29, %) | P value$^c$ |
|---|---|---|---|---|
| Control | — | 1207 ± 180 | — | — |
| Lapatinib 100 mg/kg | po, once a day, for 2 weeks | 898 ± 120 | 25.6 | 0.124 |
| Compound (1i) 200 mg/kg (11.6 mg/kg*¹) | iv, once a week, for 2 weeks | 973 ± 178 | 30.4 | 0.071 |
| Compound (1i) 300 mg/kg (17.4 mg/kg*¹) | iv, once a week, for 2 weeks | 840 ± 72 | 55.7 | 0.002 |

*¹Dose as converted to lapatinib

From Table 5, Compound (1h) exhibited an antitumor effect equivalent to that of the de-ethylated form of sunitinib, at a dose of from 4/50 to 8/50 as converted to sunitinib, relative to the dose of sunitinib. From Table 6 and FIG. 15, Compound (1i) exhibited an antitumor effect superior to lapatinib at a dose of from 11.6/100 to 17.4/100 as converted to lapatinib, relative to the dose of lapatinib.

Furthermore, it was recognized that Compound (1h) and Compound (1i) do not cause any body weight reduction at the doses described above, and it was confirmed that these compounds are also highly safe (FIG. 16).

Test Example 6

1×10⁷ cells of human breast cancer cell BT474 were transplanted into the right abdomen of a BALB/c nude mouse, and when the tumor volume reached 100 to 150 mm³, drugs were administered. The administration was implemented once a week for two weeks.

As a result, as shown in (Table 7), Compound (1j) exhibited a tumor growth inhibition ratio of 36% to 37.5%, and exhibited an effect equivalent or superior to that of paclitaxel as the control, which gave a tumor growth inhibition ratio of 29.8%. Thus, it was confirmed that Compound (1j) is a compound which can achieve an excellent balance between efficacy and safety, and that Compound (1j) also has high water-solubility per se, so that the compound can be a new therapeutic agent for a malignant tumor, which can significantly improve the means for administration in clinical settings, compared to paclitaxel that is sparingly soluble in water.

TABLE 7

| | Dosage schedule | Tumor Volume (D 23, mm³) | TGI (D 23, %) |
|---|---|---|---|
| Control | — | 392 ± 47 | — |
| Paclitaxel 5 mg/kg | iv, once a week, for 2 weeks | 275 ± 39 | 29.8 |
| Compound (1j) (200 mg/kg) | iv, once a week, for 2 weeks | 251 ± 26 | 36.0 |
| Compound (1j) (300 mg/kg) | iv, once a week, for 2 weeks | 245 ± 45 | 37.5 |

The invention claimed is:

1. A compound of Formula (1), or a salt thereof:

$$C[CH_2O(CH_2CH_2O)_mCH_2CO-R^1-R^2]_4 \quad (1)$$

wherein R¹ represents a single bond, —N(R³)(CH₂)$_{n1}$CO—, or —N(R⁴)(CH₂)$_{n2}$N(R⁵)CO(CH₂)$_{n3}$CO—, wherein R³ represents a hydrogen atom or an alkyl group; R⁴ and R⁵, which are identical or different from each other, each represent a hydrogen atom or an alkyl group, or R⁴ and R⁵ are bonded together and represent an alkylene group having 1 to 4 carbon atoms; and n1, n2, and n3, which are identical or different from each other, each represent an integer from 1 to 3;

R² represents 2'-cyano-2'-deoxy-β-D-arabinofuranosylcytosine, 3'-ethynyl-β-D-arabinofuranosylcytosine, or a group of the following formula (b), (c), (d), (e), or (f):

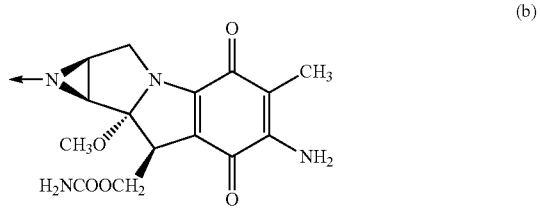

(b)

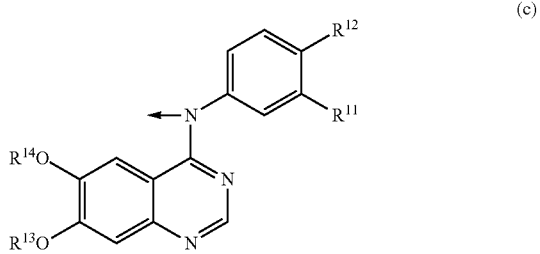

(c)

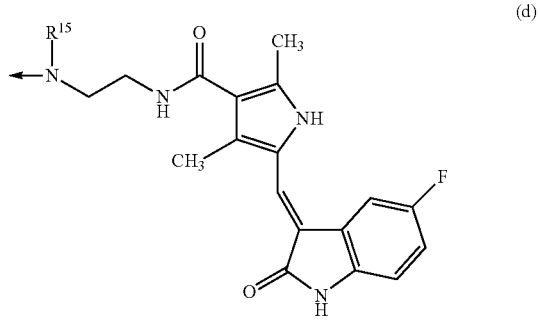

(d)

-continued (e)

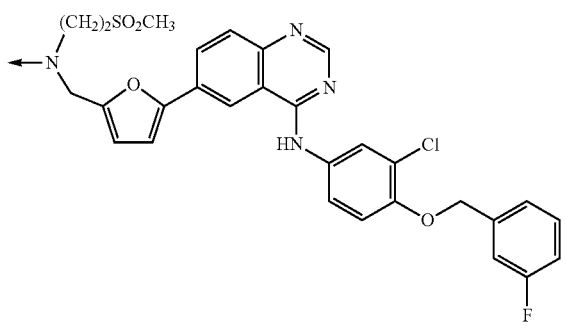

(f)

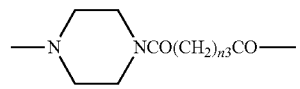

$R^{11}$ represents a halogen atom or an ethynyl group; $R^{12}$ represents a hydrogen atom or a halogen atom; $R^{13}$ represents an alkyl group or an alkoxyalkyl group;

$R^{14}$ represents an alkoxyalkyl group or a morpholinoalkyl group; $R^{15}$ represents an alkyl group; and $R^{16}$ represents a hydrogen atom or an alkanoyl group;

m represents a number of from 10 to 1,000; and an arrow represents a bonding site.

2. The compound according to claim 1, or a salt thereof, wherein $R^1$ represents a single bond, —NH(CH$_2$)$_{n1}$CO—, —NH(CH$_2$)$_{n2}$NHCO(CH$_2$)$_{n3}$CO—, or the following formula:

wherein n1, n2, and n3, which are identical or different from each other, each represent an integer from 1 to 3.

3. The compound according to claim 1 or a salt thereof, wherein $R^2$ represents 2'-cyano-2'-deoxy-β-D-arabinofuranosylcytosine.

4. The compound according to claim 3, or a salt thereof, Wherein $R^1$ represents a single bond, —NH(CH$_2$)$_{n1}$CO—, —NH(CH$_2$)$_{n2}$NHCO(CH$_2$)$_{n3}$CO—, or the following formula:

wherein n1, n2, and n3, which are identical or different from each other, each represent an integer from 1 to 3.

5. A pharmaceutical composition, comprising the compound according to claim 1, or a salt thereof, and a pharmaceutically acceptable salt.

6. A pharmaceutical composition, comprising the compound according to claim 2, or a salt thereof, and a pharmaceutically acceptable salt.

7. A pharmaceutical composition, comprising the compound according to claim 3, or a salt thereof, and a pharmaceutically acceptable salt.

8. A pharmaceutical composition, comprising the compound according to claim 4, or a salt thereof, and a pharmaceutically acceptable salt.

* * * * *